(12) United States Patent
Higham

(10) Patent No.: US 7,801,594 B1
(45) Date of Patent: Sep. 21, 2010

(54) MORPHOLOGY DISCRIMINATION BASED ON INFLECTION POINT-RELATED INFORMATION

(75) Inventor: Paul Higham, Cupertino, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 301 days.

(21) Appl. No.: 11/876,518

(22) Filed: Oct. 22, 2007

(51) Int. Cl.
*A61B 5/04* (2006.01)

(52) U.S. Cl. .................. 600/515; 600/516; 600/517; 600/518; 600/519; 600/520

(58) Field of Classification Search .......... 600/515–520
See application file for complete search history.

(56) References Cited

U.S. PATENT DOCUMENTS

| | | | |
|---|---|---|---|
| 4,905,708 A | | 3/1990 | Davies |
| 5,092,341 A * | | 3/1992 | Kelen .................. 600/515 |
| 6,580,946 B2 * | | 6/2003 | Struble .................. 607/23 |
| 6,687,540 B2 * | | 2/2004 | Marcovecchio .............. 607/5 |
| 7,123,953 B2 * | | 10/2006 | Starobin et al. ............. 600/516 |
| 7,225,014 B1 * | | 5/2007 | Province .................. 600/516 |
| 7,630,521 B2 * | | 12/2009 | Kim et al. .................. 382/115 |
| 2003/0199779 A1 * | | 10/2003 | Muhlenberg et al. ........ 600/513 |
| 2006/0235315 A1 * | | 10/2006 | Akselrod et al. ........... 600/509 |

\* cited by examiner

*Primary Examiner*—Carl H Layno
*Assistant Examiner*—Paula J Stice
(74) *Attorney, Agent, or Firm*—Theresa A. Takeuchi; Steven M. Mitchell

(57) ABSTRACT

A morphology discrimination scheme extracts shape characteristics from cardiac signals and identifies an associated cardiac condition based on the shape characteristics. For example, internal data structures may be updated to match the shape characteristics of a known condition (e.g., a patient's normal sinus rhythm). Similarly acquired shape characteristics obtained in conjunction with a later event (e.g., QRS complexes acquired during a tachycardia episode) may be compared with the previously stored shape characteristics to characterize the later event. In some aspects the shape characteristics relate to inflection points of cardiac signals.

17 Claims, 15 Drawing Sheets

| UB | 2 | -1 | 3 | -1 | 1 |
|---|---|---|---|---|---|
| LB | 2 | -1 | 3 | -1 | 1 |

|  |  |  |  |  |  |
|---|---|---|---|---|---|
| 0 |  |  |  |  |  |
| 1 |  | 1 |  | 1 | 1 |
| 2 | 1 |  |  |  |  |
| 3 |  |  | 1 |  |  |

| UB | 2 | -1 | 3 | -1 | 1 |
|---|---|---|---|---|---|
| LB | 2 | -1 | 3 | -1 | 1 |

904A

| 3 | -2 | 2 |
|---|---|---|

| 3 | -2 | 2 |
|---|---|---|

| UB | 2 | -1 | 3 | -1 | 2 |
|---|---|---|---|---|---|
| LB | 2 | -1 | 3 | -2 | 1 |

|  |  |  |  |  |  |
|---|---|---|---|---|---|
| 0 |  |  |  |  |  |
| 1 |  | 1 |  | 1 | 1 |
| 2 | 1 |  |  | 1 | 1 |
| 3 |  |  | 2 |  |  |

MORPHOLOGY DISCRIMINATION BASED ON INFLECTION POINT-RELATED INFORMATION

TECHNICAL FIELD

This application relates generally to morphology discrimination and more specifically, but not exclusively, to discrimination of cardiac signals based on inflection point-related information.

BACKGROUND

Morphology discrimination may be used in conjunction with cardiac therapy to distinguish one type of cardiac signal from another. For example, a heartbeat waveform may have a particular shape when the heart is beating in a normal manner and different shape when the heart is beating in an irregular manner (e.g., during arrhythmia). Accordingly, a cardiac device may acquire electrocardiogram signals representative of cardiac waveforms over time and use morphology discrimination to determine whether the shapes of the acquired signals indicate a regular or irregular heartbeat.

In general, a conventional morphology discrimination scheme may involve generating a template corresponding to how a given set of data is expected to appear and comparing a candidate set of data with the template to characterize the candidate set of data. For example, a template may consist of a mean and an associated standard deviation derived from several sets of data that are known or expected to be representative of some condition. Then, when it is desired to determine whether a candidate set of data also is associated with that condition, the candidate set of data is compared with the template. For example, the candidate set of data may be cross correlated with the template to determine whether this set of data falls within a range of values defined by the template.

Some conventional cardiac morphology discrimination schemes discriminate between different cardiac signals by comparing the peaks of the cardiac signals. Here, a cardiac device may generate a morphology template by collecting information regarding the magnitude (e.g., relative to a baseline) of the peaks of a set of QRS complexes that are known or expected to correspond to a given cardiac condition. At some later point in time, the device may compare the peaks of current QRS complexes with the morphology template to categorize the patient's current condition.

As a specific example, cardiac signals associated with ventricular tachycardia may be distinguished by their shape from cardiac signals associated with other arrhythmias that resemble normal sinus rhythm (e.g., super-ventricular tachycardia). In such a case, the morphology template may be defined to represent cardiac signals as they appear during normal sinus rhythm. The morphology discrimination process may then determine whether a given set of cardiac signals are associated with ventricular tachycardia or these other arrhythmias by comparing the cardiac signals to the template.

In general, morphology discrimination schemes such as these may rely on an assumption that the template information is relatively constant. Hence, the accuracy of such schemes may depend on the degree to which the signals used to generate the template fluctuate and on the sensitivity of any cardiac device component that is used to generate the electrocardiogram. For example, if a cardiac signal has peak values (either local maxima or local minima) that are close to the baseline (e.g., zero), small changes in the baseline value may affect the number of peaks detected. As a result, a measure of similarity that depends on this comparison may find quite different signals whose shapes should be considered very similar, if not identical. Accordingly, a need exists for more effective techniques for discriminating between cardiac signals.

SUMMARY

A summary of several sample aspects of the disclosure and embodiments of an apparatus constructed or a method practiced according to the teaching herein follows. It should be appreciated that this summary is provided for the convenience of the reader and does not wholly define the breadth of the disclosure. For convenience, one or more aspects or embodiments of the disclosure may be referred to herein simply as "some aspects" or "some embodiments."

The disclosure relates in some aspects to a morphology discrimination scheme that extracts shape information from electrocardiogram signals and identifies an associated cardiac condition based on this shape information. Here, baseline shape information is acquired by sampling cardiac signals associated with a known or expected cardiac condition. This baseline information may then be compared with information derived from other cardiac signals to characterize the other cardiac signals. For example, the baseline information may be derived from cardiac signals during normal sinus rhythm and the other cardiac signals collected during an arrhythmia. In this case, the morphology discrimination scheme may be used to distinguish between ventricular tachycardia and other conditions (e.g., super-ventricular tachycardia) that have waveforms that are similar in shape to sinus rhythm waveforms.

The disclosure relates in some aspects to morphology discrimination that is based on inflection points in a cardiac signal. For example, QRS complexes associated with a known cardiac condition (e.g., normal sinus) may be processed to obtain information relating to the inflection points of each complex. In some embodiments this information comprises a derivative of the inflection point information. The inflection point-related information may then be used to generate a baseline template for the morphology discrimination process. In a similar manner inflection point information may be generated from candidate QRS complexes that are to be compared with the baseline template. The cardiac condition associated with these candidate QRS complexes may then be characterized based on the results of the comparison.

In some embodiments the morphology discrimination process involves generating a matrix from a series of vectors, each of which is derived from the inflection points of a given heartbeat signal (e.g., at least a portion of a QRS signal) associated with normal sinus rhythm. Here, the derivative of the electrocardiogram signal is generated to provide a set (e.g., a vector) of optima associated with the signal, where each of the optima relates to a corresponding inflection point. The optima of the set are then ranked according to magnitude to provide a rank vector. Finally, the derivative of the rank vector is generated to provide another vector having elements indicative of the magnitude of the change in the ranking of each of the inflection points.

The resulting vectors are then used to generate a matrix that includes information associated with a shape distribution of the patient's normal sinus rhythm. In some aspects the matrix may comprise a statistical summary of the vectors. For example, the matrix may comprise a series of tallies that indicate the number of times a particular magnitude (e.g., associated with a given row in the matrix) occurred at a given position (e.g., associated with a given column of the matrix) in the vectors that were used to generate the matrix. Thus, the entries in the matrix may indicate the frequency and relative position at which certain inflection point-related characteristics tend to occur during normal sinus rhythm.

Here, as each new vector is added to the matrix an appropriate alignment is selected for the vector to ensure that the elements of the vector correlate to the greatest degree with the current elements of the matrix. Here, the size of the matrix may be expanded as necessary to accommodate the various alignments of the vectors that make up the matrix. However, certain constraints may be placed on the alignment selection process to prevent the matrix from becoming too large. In addition, the matrix may be recalibrated over time to ensure that the matrix accurately represents the patient's normal sinus rhythm.

A discrimination operation may then use the matrix to score QRS complexes associated with a given event (e.g., a potential tachyarrhythmia). For example, in a similar manner as described above, the discrimination operation generates one or more vectors comprising inflection point-related information that is derived from associated electrocardiogram signals. Each resulting vector is then compared with the matrix by first determining the best alignment for comparing the vector with the matrix, then calculating a score that is indicative of the frequency at which the elements of the vector occur at similar relative positions in the matrix. Such a score may thereby indicate, for example, a probability relating to a degree to which the shape of a candidate QRS complex is indistinguishable from sinus.

If this score indicates a sufficient correlation between one or more candidate vectors and the matrix, a determination may be made that cardiac signals associated with the candidate vector or vectors is sufficiently similar to the sinus cardiac signals that were used to generate the matrix. A corresponding indication is then generated and appropriate therapy is prescribed for the patient based on the results of this determination.

As mentioned above, in some embodiments the teachings herein may be employed to distinguish ventricular tachycardia from super-ventricular tachycardia. In this case, the patient's heart may be monitored over time to identify any times at which the heart experiences an arrhythmia. In the event the arrhythmia is identified as a tachycardia event, the morphology discrimination process taught herein may be invoked. Thus, vectors generated from the current or recent cardiac signals may be compared with a matrix generated from cardiac signals associated with sinus rhythm. If the vectors are similar to the matrix a determination is made that the underlying cardiac signals are sinus in nature (e.g., super-ventricular tachycardia). Hence, an appropriate therapy (e.g., pacing therapy) may be administered for this condition. In contrast, if the vectors are not sufficiently similar to the matrix a determination is made that the underlying cardiac signals are associated with ventricular tachycardia. In this case, different therapy (e.g., a shock) may be administered to the patient.

A discrimination scheme as described above may advantageously provide a stable enough signature to distinguish between a series of sinus beats and a series arising from ventricular tachycardia. This may be accomplished, in part, through the use of a shape characteristic vector that is affected neither by changes in the baseline voltage, nor by the time dilation of the signal. Moreover, such a scheme may reliably discriminate between shapes even when the shapes include relatively small divots.

BRIEF DESCRIPTION OF THE DRAWINGS

These and other features, aspects, and advantages will be more fully understood when considered with respect to the following detailed description, appended claims and accompanying drawings, wherein:

FIG. 4, including

FIG. 9, including FIGS. 9A, 9B, and 9C, depicts simplified examples of upper and lower bounds vectors and matrices;

FIG. 11, including

Figure 1:
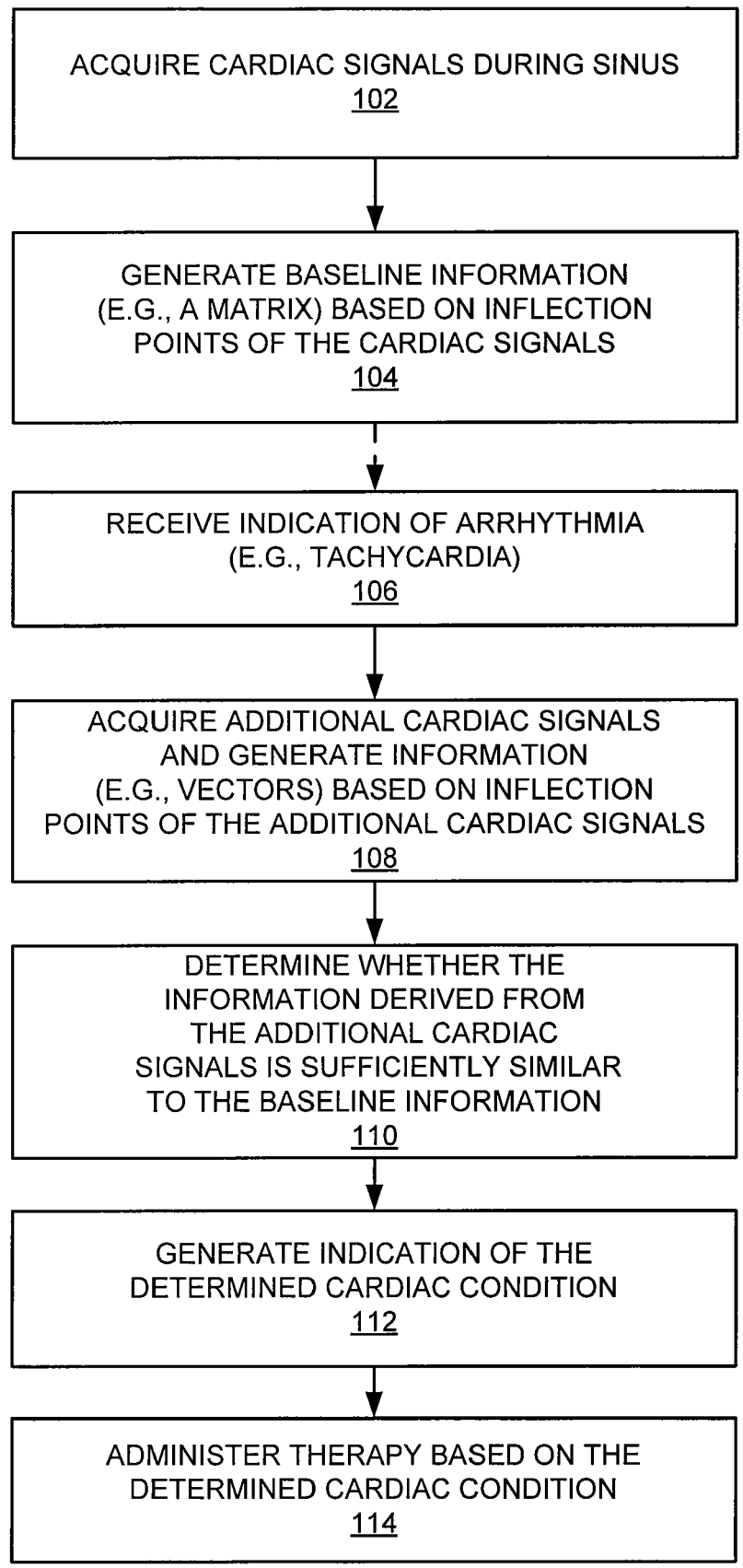
FIG. 1 is a simplified flowchart of an embodiment of operations that may be performed to identify a cardiac condition through analysis of inflection points of cardiac signals.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teaching herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

The flowchart of FIG. 1 provides an overview of several operations that may be performed to discriminate cardiac signal through the use of inflection point-based analysis. Briefly, these operations involve generating inflection point-related baseline information representative of cardiac activity during a given state (e.g., sinus), collecting additional inflection point-related information representative of cardiac activity at later point in time, and determining the extent to which the additional information matches the baseline information. In this way, the current condition of the patient may be determined so that appropriate therapy is provided for the patient.

The discussion that follows relates to a specific example where an implantable device analyzes cardiac waveforms to determine whether a patient is experiencing ventricular tachycardia or super-ventricular tachycardia. It should be appreciated, however, that the concepts that follow may be equally applicable to other shape discrimination procedures and may be performed, at least in part, by non-implantable devices.

Here, super-ventricular tachycardia relates to tachycardia that originates above the ventricles. For example, super-ventricular tachycardia may originate in an atrium or the atrio-ventricular ("AV") node.

In general, it is desirable to determine whether a tachycardia event is ventricular tachycardia or super-ventricular tachycardia so that appropriate therapy may be prescribed for the patient. For example, a common treatment for ventricular tachycardia involves delivering a high voltage shock to the heart. In contrast, a high voltage shock may not be a desirable or effective treatment for super-ventricular tachycardia. Rather, treatment of super-ventricular tachycardia may involve pacing the heart or some other less intrusive procedure. Consequently, the application of a high voltage shock in this case may result in unnecessary discomfort for the patient. Moreover, such a shock may consume a relatively significant amount of power, thereby unnecessarily reducing the operating life of the battery of the implantable device.

In some aspects the tachycardia discrimination techniques described herein are based on a determination that cardiac waveforms associated with super-ventricular tachycardia may in some respects more closely resemble waveforms associated with normal sinus than cardiac waveforms associated with ventricular tachycardia. Accordingly, as described below a tachycardia event may be identified as either ventricular tachycardia or super-ventricular tachycardia by comparing certain aspects of a one or more cardiac waveforms acquired during the event with certain aspects of one or more known sinus waveforms.

Blocks 102 and 104 of FIG. 1 relate to acquiring baseline information for the discrimination process. Block 102 represents operations where an implantable device acquires cardiac signals during normal sinus. For example, the device may generate intracardiac electrogram ("IEGM") signals based on cardiac activity sensed during normal sinus conditions. At block 104 the implantable device processes the cardiac signals to generate the baseline information. The device then stores the baseline information in a memory device for use during subsequent discrimination operations.

Figure 2:
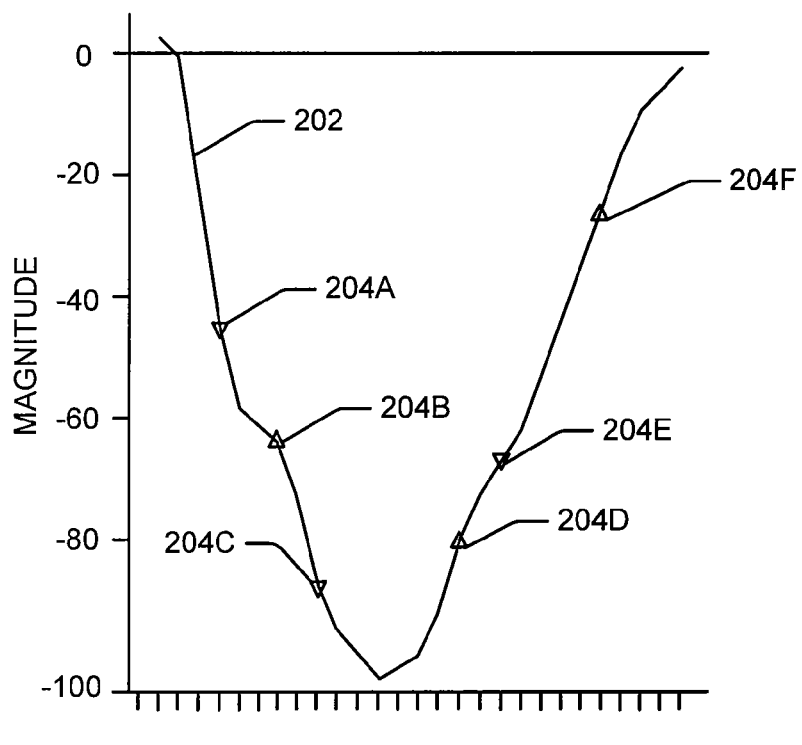
FIG. 2 is a simplified diagram of a cardiac waveform.

In some aspects the baseline information relates to inflection points of the acquired cardiac signals. For example, FIG. 2 depicts a simplified representation of a cardiac waveform 202 where amplitude is plotted versus time. The waveform 202 may represent, for example, a portion of a QRS complex acquired by the implantable device during normal sinus rhythm. For illustration purposes, the waveform 202 is represented as a continual waveform where lines connect each of the sample points, rather than as a plot of sample points.

Inflection points in the waveform 202 are represented by the arrows 204A-204F (collectively, "arrows 204"). For example, at a point in time corresponding to the downward-pointing arrow 204A the absolute magnitude of the slope of the waveform 202 starts to decrease. Conversely, at a point in time corresponding to the upward-pointing arrow 204B the absolute magnitude of the slope of the waveform 202 starts to increase. In other words, the inflection points correspond to the points where the concavity of the waveform 202 switches from concave down to concave up (a downward-pointing arrow), and vice versa (an upward-pointing arrow).

As discussed below, information relating to such inflection points may be used to determine whether a given waveform is similar or to dissimilar to another waveform (e.g., a set of data representative of the waveform). For example, a signal may be sufficiently characterized based on information relating to the magnitude and direction of the inflection points.

An inflection point-based discrimination technique may advantageously provide a more accurate way of discriminating between waveforms. For example, some conventional morphology discrimination schemes distinguish signals by integrating the waveforms and comparing the corresponding integration data (e.g., area under the curve) for each waveform. Consequently, schemes such as these may not take into consideration information relating to the magnitude and timing of all peaks and valleys of the waveform or other information that may more accurately represent the particular shape of the waveform.

Figure 3:
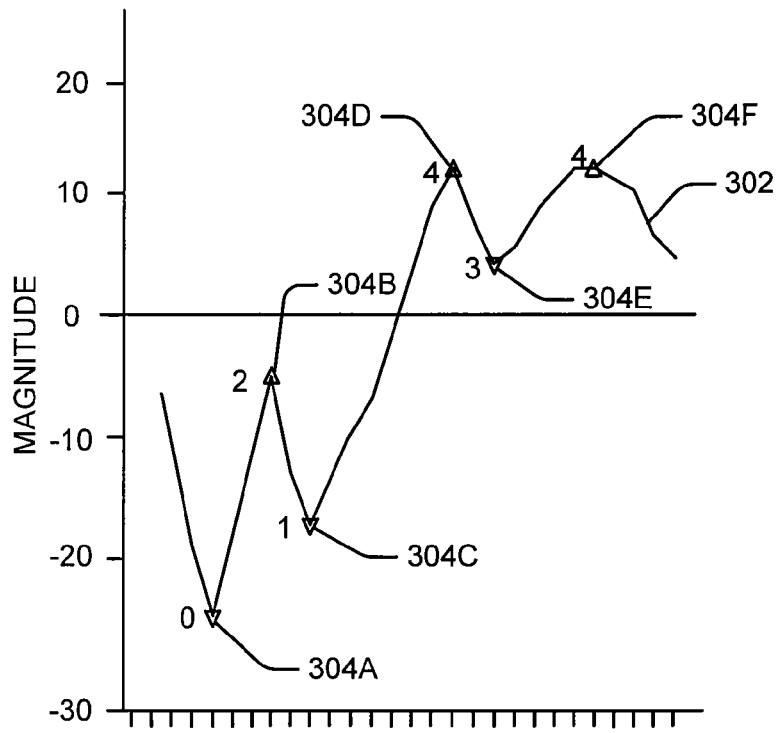
FIG. 3 is a simplified diagram of a derivative of the cardiac waveform of FIG. 2.

In some aspects inflection point-related information is obtained by calculating the derivative of the waveform. FIG. 3 depicts a waveform 302 that corresponds to a derivative of the waveform 202 of FIG. 2. Here, local optima (minimums and maximums) of the waveform 302 correspond to the inflection points 204 of FIG. 2. These optima are designated in FIG. 3 by a series of arrows 304A-304F (collective, arrows 304) that correspond to arrows 204A-204F, respectively. For example, the arrow 304A corresponds to the inflection point of arrow 204A. In FIG. 3, a downward-pointing arrow corresponds to a local minimum and an upward-pointing arrow corresponds to a local maximum. In addition, the relative magnitudes of the optima relate to the magnitude of the gradient at each inflection point 204.

In practice, a discrete analog of differential calculus may be employed to obtain the information represented by FIG. 3. For example, an implantable device typically stores the signal information corresponding to FIG. 2 in digital form. Hence, in this case, a digital analog of a derivative may be employed to obtain a derivative of this data. For example, a discrete derivative of a signal $S=\{x_0, x_1, \ldots, x_n\}$ is defined as $\{x_1-x_0, x_2-x_1, \ldots, x_n-x_{n-1}\}$ which may be seen as a finite impulse response digital filter. For a fixed sample rate this formula may give the best approximation to the instantaneous rate of change in the original analog signal.

To find the local optima of a signal, the places where the discrete derivative has changed sign are identified. Here, a change from positive to negative indicates the presence of a local maximum while a change from negative to positive indicates at local minimum.

As shown in FIG. 3, a digital derivative may thus be calculated for each sampling point of the waveform 202 (including the inflection points 204) whereby the derivative corresponds to the difference between the magnitudes of a given sampling point and a previous sampling point. Here, it should be appreciated that in the discrete analog of the limiting procedure that defines the derivative, the delta t term in the denominator becomes the sampling interval, which is a constant over all calculations and can be factored out of all of them. Thus, the derivative at an inflection point is simply the difference between the magnitude of the inflection point and the magnitude of the previous sample in FIG. 2. For illustration purposes, the derivative of FIG. 3 is represented as a continual waveform where lines connect each of the derivative points, rather than as a plot of derivative points.

Advantageously, the derivative of a cardiac signal may provide certain information that may be used to more accurately discriminate between different waveforms. For example, as compared to the original waveform the number of local optima is typically larger in the derivative of the waveform. In addition, the number of local optima may have a small variance over all observed waveforms (e.g., QRS complexes) of the derivative. Also, the relative positions of the local optima of the derivative may not change from complex to complex even when the amplitude of the waveform varies considerably.

For example, the duration and/or magnitude of a QRS complex of a patient may change as a result of an increase or decrease in the activity level of the patient or for some other reason. However, assuming that there has not been a significant cardiac event such as an arrhythmia, the basic shape of the QRS complex may remain the same under these or other circumstances. As a specific example, even though the duration of a waveform may change over time, the relative times and characteristics (e.g., magnitude of the gradient) of the inflection points of the waveform may remain relatively constant (e.g., in terms of a relative percentage of the total time period). Similarly, changes in the magnitude of a waveform may not affect a relative times and characteristics of the inflection points. Again, it is assumed here that the patient's basic cardiac condition has not changed. The above attributes of inflection points are further illustrated by the example of FIG. 4 which shows how relatively minor changes in the shape of a waveform (e.g., minor oscillations in voltage) may be properly accounted for through the used of inflection point-based information.

Figure 4A:
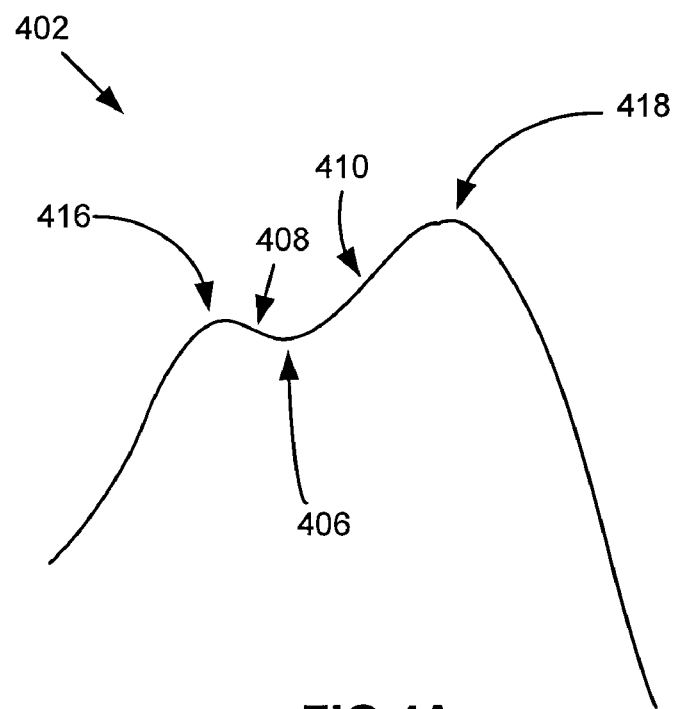
FIGS. 4A and 4B, depicts simplified examples of divots in cardiac waveforms.
Figure 4B:
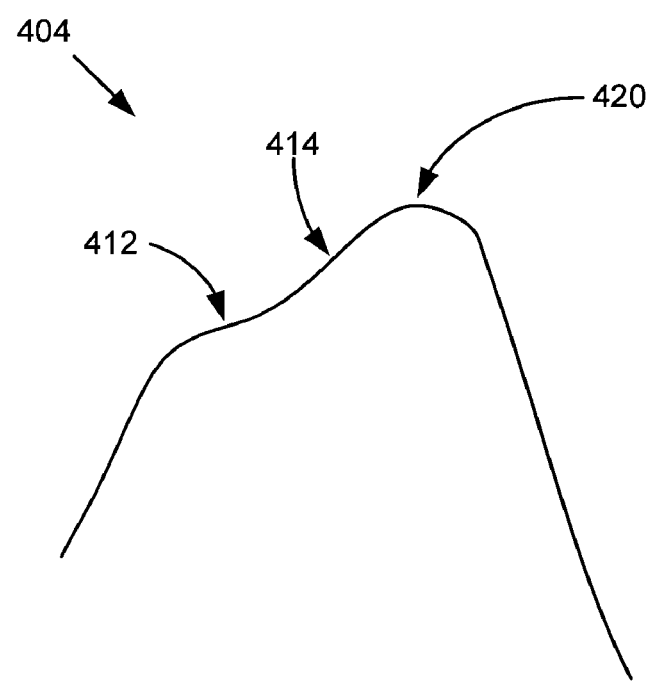

FIG. 4A depicts a waveform 402 representing portion of a QRS complex that has a divot-like characteristic 406 (hereafter referred to as a "divot") that may be the result of, for example, non-synchronous contractions of the right and left ventricles. In general, the duration of this inter-ventricular delay may vary over time. For example, the delay may be characterized by a random distribution over time. Hence, at some point in time the patient's QRS complex may have the shape of the waveform 404 of FIG. 4B where the divot is diminished somewhat due to, for example, a shorted delay between the contractions of the right and left ventricles.

Advantageously, inflection point-based discrimination as taught herein may classify the waveforms 402 and 404 as being sufficiently similar. For example, the waveform 402 has a first inflection point (as indicated by the arrow 408) followed by a second inflection point (as indicated by the arrow 410). Here, the first inflection point 408 corresponds to a change from concave down to concave up and the second inflection point 410 corresponds to a change from concave up to concave down. In a similar manner, the waveform 404 has a first inflection point (as indicated by the arrow 412) followed by a second inflection point (as indicated by the arrow 414). Again, the first inflection point 412 corresponds to a change from concave down to concave up and the second inflection point 414 corresponds to a change from concave up to concave down.

In contrast, a morphology discrimination scheme that distinguishes signals by comparing the local peaks of the signals may determine that the waveforms 402 and 404 are not sufficiently similar. For example, this type of scheme may determine that the signals are different because the waveform 402 has two local peaks 416 and 418 while the waveform 404 only has one local peak 420.

As will be discussed in more detail below, the derivative of the cardiac signal is used to provide baseline information for the discrimination process. In some implementations the baseline information is maintained in the form of a matrix. For example, the matrix may be formed by consolidating information from a series of vectors each of which includes derivative-related information associated with a given sinus waveform.

Referring again to FIG. 1, as represented by block 106 at some point in time a decision is made to analyze cardiac signals to determine whether an arrhythmic episode (or some other condition) has occurred or is occurring. For example, in some implementations a component of an implantable device that continually monitors cardiac activity may, at some point, indicate that the patient is experiencing tachycardia.

As represented by block 108, in response to the indication of block 106 the implantable device acquires cardiac signals corresponding in time to the tachycardia event. In a typical implementation (e.g., when the device is a cardiac stimulation device), the implantable device will continually acquire and store cardiac signal information (e.g., IEGMs). Hence, the signals corresponding to the tachycardia event may be readily available (e.g., already stored in a memory device).

The implantable device then processes these additional cardiac signals to extract inflection point-related information (e.g., as discussed above in conjunction with block 104). Thus, in some implementations this operation involves generating a series of vectors, where each of the vectors is associated with a given heartbeat (e.g., a unique QRS complex) and includes information relating to a derivative of the associated heartbeat waveform.

As represented by block 110, the implantable device scores the candidate information from block 108 using the baseline information generated at block 104. Based on this score, the device generates an indication of the corresponding cardiac condition at block 112. As mentioned above, this may involve generating an indication as to whether a detected arrhythmia is ventricular tachycardia or super-ventricular tachycardia. As represented by block 114, in some implementations the implantable device will administer appropriate therapy based on the identified cardiac condition.

Figure 7:
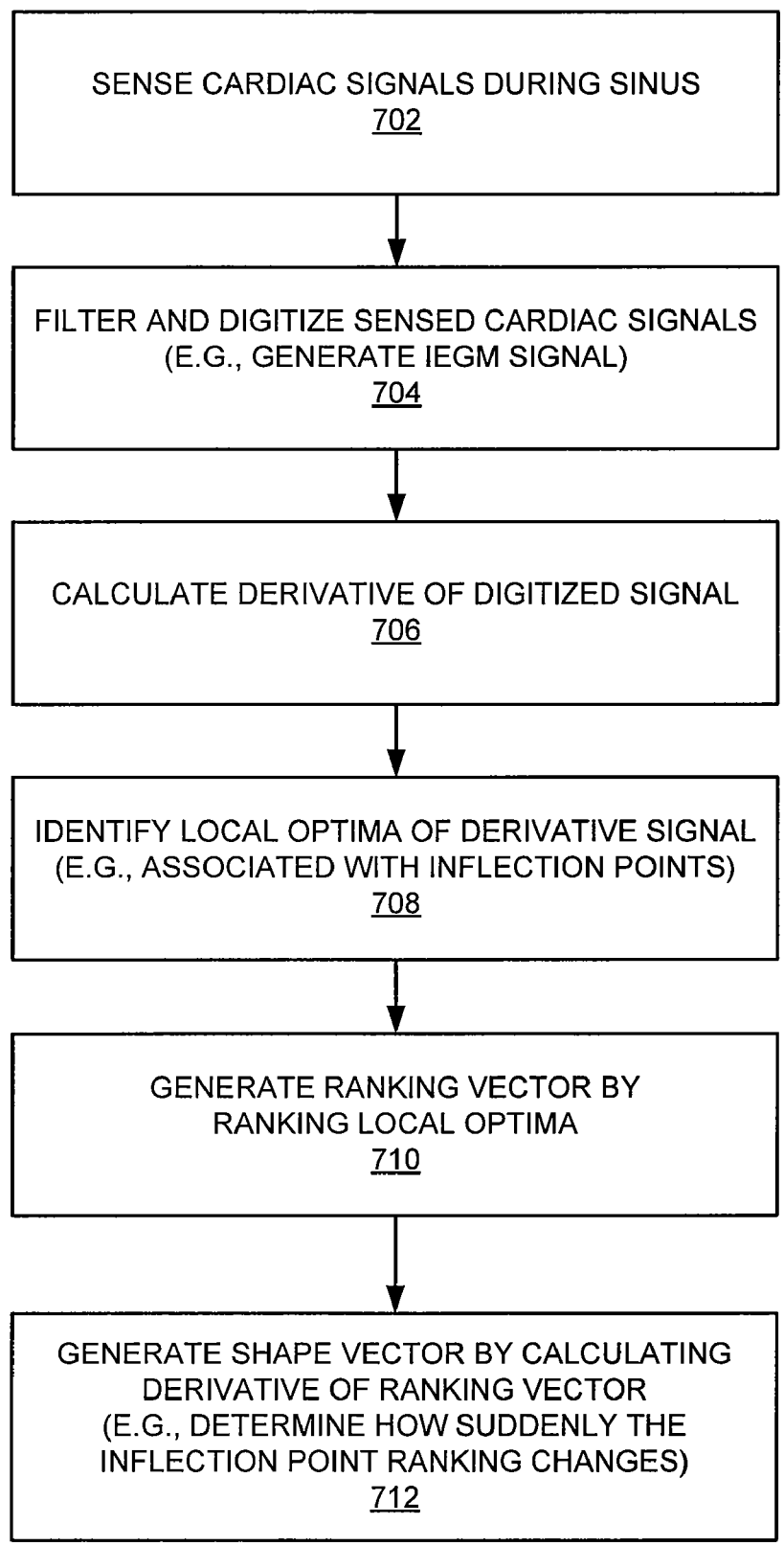
FIG. 7 is a simplified flowchart of an embodiment of operations that may be performed to provide a shape vector.
Figure 8:
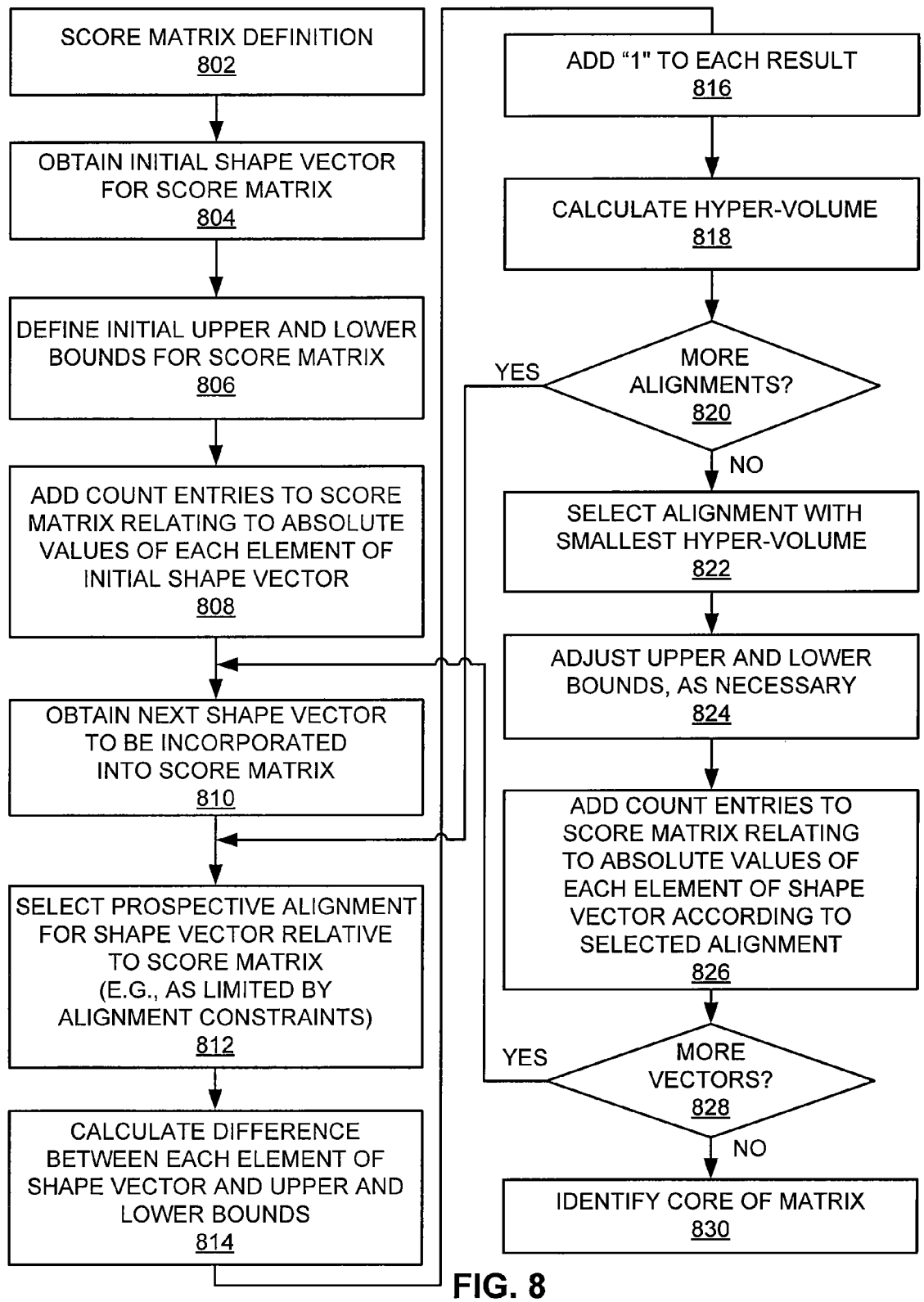
FIG. 8 is a simplified flowchart of an embodiment of operations that may be performed to provide a score matrix.
Figure 14:
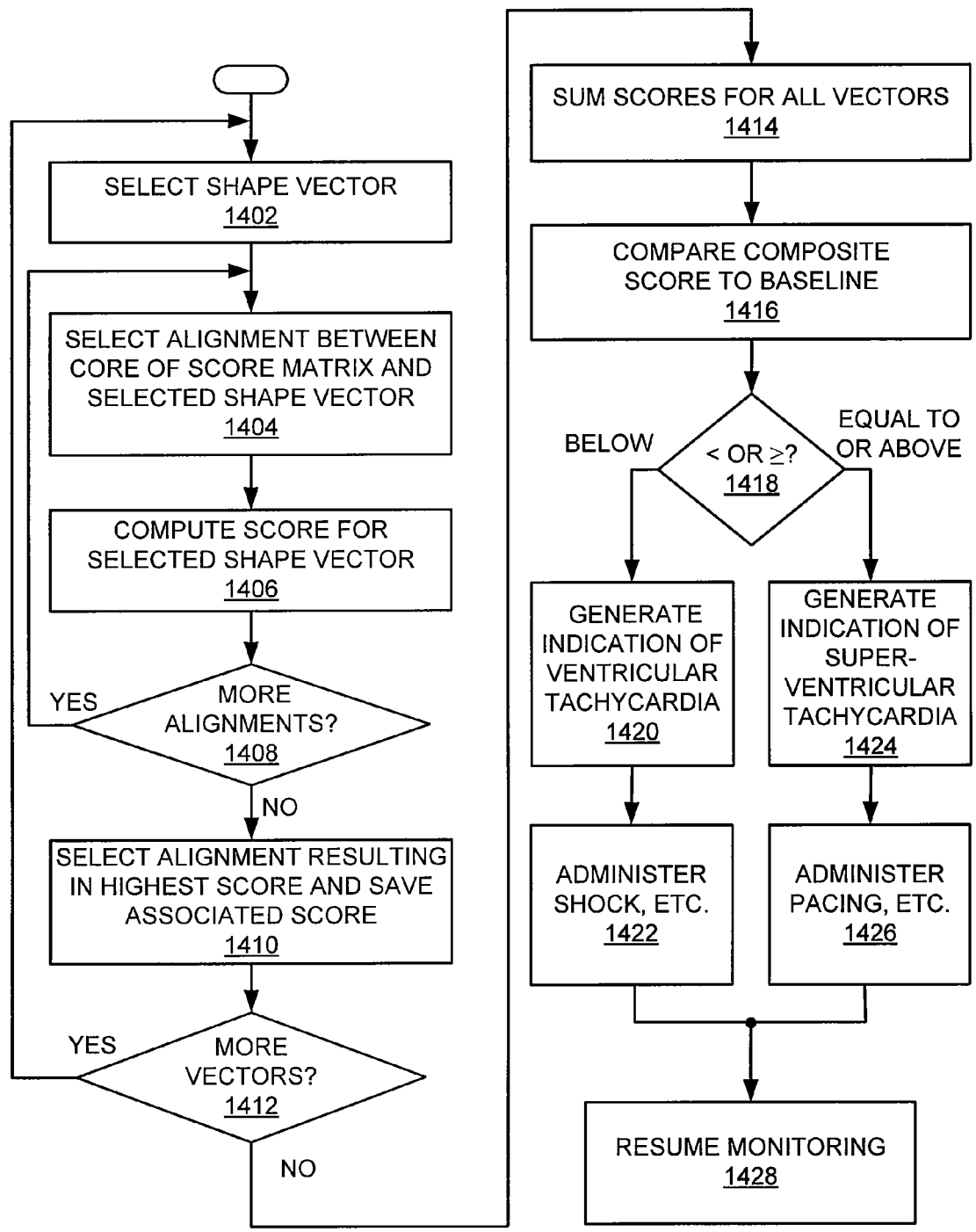
FIG. 14 is a simplified flowchart of an embodiment of morphology discrimination operations that utilize a score matrix.

These and other operations will be discussed in detail in conjunction with the flowcharts of FIGS. 5, 7, 8, and 14 and other related drawings. Briefly, FIG. 5 describes, at a high level, a discrimination operation that utilizes shape vectors and a score matrix to distinguish ventricular tachycardia and super-ventricular tachycardia. FIG. 7 illustrates several operations that may be performed to generate a shape vector. FIG. 8 illustrates several operations that may be performed to generate a score matrix. FIG. 14 illustrates several operations that may be performed to compare shape vectors associated with a potential tachycardia with a score matrix.

Figure 5:
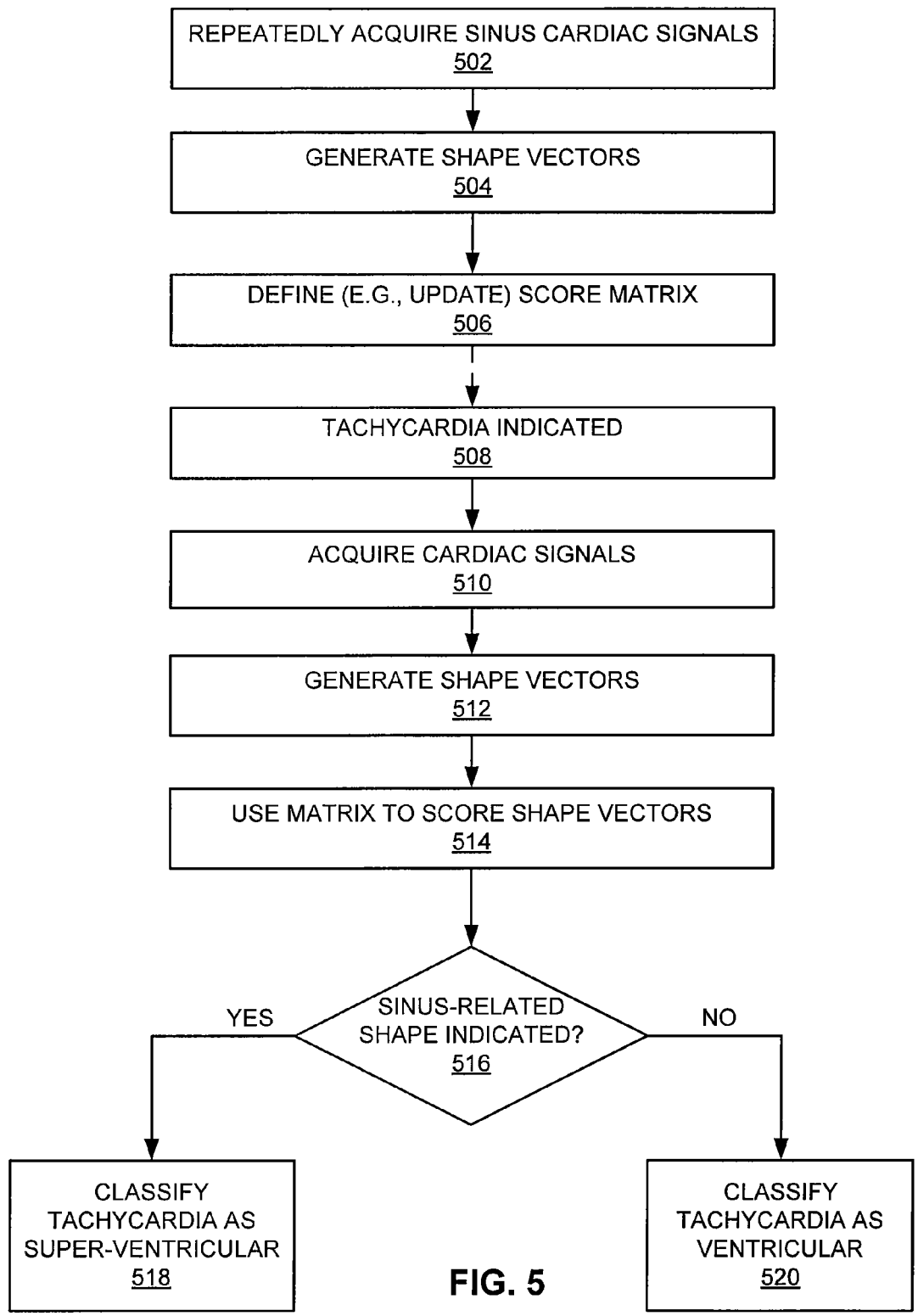
FIG. 5 is a simplified flowchart of an embodiment of operations that may be performed to identify ventricular tachycardia or super-ventricular tachycardia.
Figure 6:
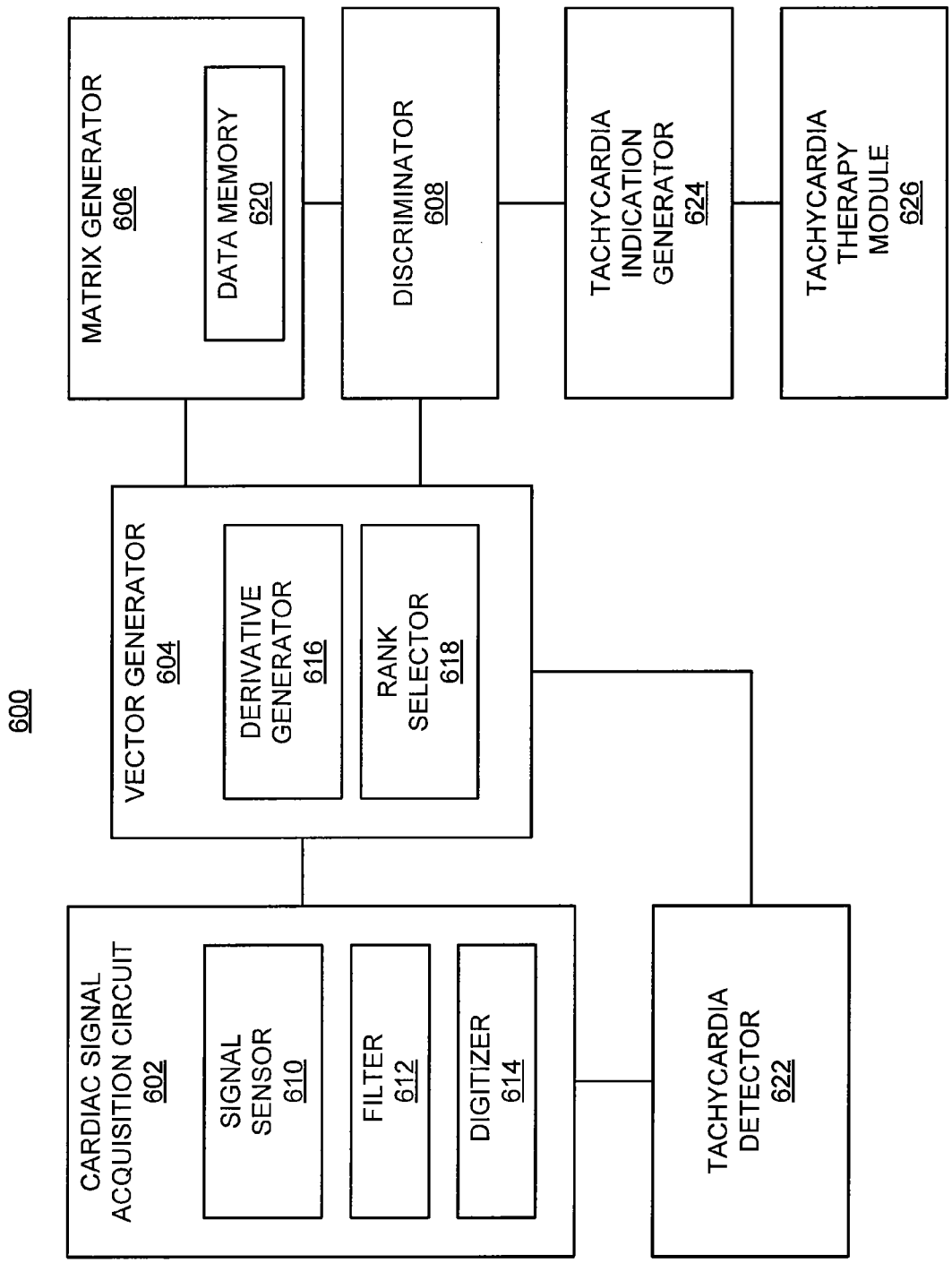
FIG. 6 is a simplified block diagram of an embodiment of components that may be used to identify and treat tachycardia.

For convenience, the operations of FIGS. 5, 7, 8, and 14 (or any other operations discussed or taught herein) may be described as being performed by specific components (e.g., an implantable device including the components of FIG. 6). It should be appreciated, however, that these operations may be performed by other types of components and may be performed using a different number of components. It also should be appreciated that one or more of the operations described herein may not be employed in a given implementation.

Referring initially to FIG. 6, a discrimination system 600 includes several functional components that may be implemented in, for example, an implantable device to perform discrimination operations as taught herein. Briefly, the system 600 includes a cardiac acquisition circuit 602 for acquiring cardiac signals (e.g., IEGM signals), a vector generator 604 for generating ranking vectors and shape vectors, a matrix generator 606 for generating a matrix, a discriminator 608 for comparing vectors with a matrix, and several other associated components.

Referring now to FIG. 5, as represented by block 502, the acquisition circuit 602 acquires cardiac signals on a regular basis. For example, as discussed below in conjunction with FIG. 7 the acquisition circuit 602 may continually generate IEGM signals (e.g., in the form of data) and store these signals in a data memory.

As represented by block 504, the vector generator 604 may generate shape vectors that are used to generate baseline information (e.g., a score matrix) for the discrimination operation. For example, a shape vector may be generated for each QRS complex in a consecutive series of QRS complexes. This set of vectors may be generated once a week, once every few weeks, or at other suitable times.

Several sample operations that may be performed in conjunction with the generation of a shape vector will be described in conjunction with FIG. 7. Blocks 702 and 704 describe, in more detail, the operations of block 502 above relating to acquiring data to be used to generate a given vector. Blocks 706-710 relate to generating a ranking vector from the acquired data. Block 712 relates to generating a shape vector from the ranking vector.

As mentioned above, the vector generator 604 may generate a given shape vector based on a cardiac signal associated with a heartbeat. Accordingly, as represented by block 702, the acquisition circuit 602 may include or be associated with one or more signal sensors 610 that sense cardiac signals. In addition, the acquisition circuit 602 may include one or more filters 612 for filtering the sensed signals. A digitizer 614 may then digitize the sensed and filtered signals to generate IEGM data (e.g., as represented by the waveform of FIG. 2).

As mentioned above, the acquisition circuit 602 may acquire the signals during sinus. To this end, the acquisition circuit 602 may include a signal analysis component (not shown) that monitors one or more physiological parameters to determine when a normal sinus condition exists. For example, the signal analysis component may calculate the current heart rate, perform some form of filtering and threshold detection, perform some form of morphology discrimination, monitor other physiological parameters (e.g., pressure, respiration, or some other suitable parameter), perform some other operation, or perform some combination of two or more of these operations.

At block 706 a derivative generator 604 generates a derivative signal by taking the digital derivative of the cardiac waveform associated with a given heartbeat (e.g., comprising a single QRS complex). For example, the function of the derivative generator 616 may involve generating a set of derivative points as shown, for example, in FIG. 3.

At block 708, the vector generator 604 identifies the local optima, ordered in time, of the derivative signal generated at block 706. Referring again to the example of FIG. 3, at this step the vector generator 604 identifies the local minimums and maximums 304 that correspond to the inflection points 204 of the cardiac waveform 202.

In some embodiments, sufficient information may be obtained for the discrimination procedure simply from the relative positions of the different magnitudes of optima. In other words, the discrimination procedure may adequately distinguish different waveforms based on the relative magnitudes and positions of associated optima, as opposed to the actual magnitude of the optima. Moreover, by not relying on the actual magnitudes of the waveform, variations in the magnitudes of the waveforms (as opposed to the shapes of the waveforms) may have less effect on the discrimination process. In other words, the process may correctly identify as similar two waveforms that have different magnitudes but have the same basic shape.

Accordingly, at block 710, a rank selector 618 assigns a rank to each of the local optima of the derivative signal generated at block 706 to generate a ranking vector. Here, the rankings indicate the relative magnitudes of the change in gradient at each inflection point. For example, in FIG. 3 sample rank values of the local optima 304 are listed next to each of the local optima 304. Here, since the local minimum 304A has the smallest magnitude derivative value of this set of optima, it is assigned a rank of 0. Local minimum 304C is assigned a rank of 1 since it has the next highest derivative value. Local maximum 304B is then assigned a rank of 2, local minimum 304E is assigned a rank of 3, and local maximums 304D and 304F, being equal in value, are assigned the same rank: rank 4. Thus, an example of a ranking vector that may be associated with FIG. 3 is: <0, 2, 1, 4, 3, 4>.

As compared to other discrimination techniques, a derivative-based technique employing ranking may be less sensitive to problems associated with comparing a cardiac signal to a threshold. For example, a threshold may change due to fluctuations relating to the operation of the hardware (e.g., sensors and threshold detector) of the device. Thus, a discrimination technique that bases its discrimination decision on such a threshold (e.g., techniques that rely on the identification of peaks in the signal) may be significantly impacted by fluctuations relating to the threshold. Moreover, some schemes may depend on a baseline voltage of an IEGM to be fixed at zero. These schemes may thus be adversely affected by any upward or downward displacement (e.g., changes in the DC level) of the waveforms. In contrast, a discrimination operation based on ranked inflection point information as taught herein may not be as adversely impacted by the above conditions.

At block 712, the vector generator 604 generates a shape vector based on the ranking vector generated at block 710. Specifically, in this example the derivative generator 604 generates another vector of derivative information by taking the digital derivative of the ranking vector information. In essence this derivative information indicates how suddenly the inflection point-based rankings change. Continuing with the above example, the first element in the shape vector is 2−0=2; the second element is 1−2=−1; the third element is 4−1=3; the fourth element is 3−4=−1; and the fifth element is 4−3=1. Thus, the shape vector in this example is: <2, −1, 3, −1, 1>. Here it may be observed that the rank of a local maximum must be larger than the rank of any adjacent local minimum. Consequently, the components of the shape vector are never zero and alternate in sign.

It should be appreciated that the ranking and shape vectors contain the same basic information. That is, either one of these vectors may be derived from the other. Use of the shape vector may, however, provide certain advantages. For example, the shape vector includes one fewer element than the ranking vector. Hence, less data memory may be required in embodiments that use the shape vector. Moreover, the elements of the shape vector alternate in polarity which, as discussed below, facilitates certain efficiencies when merging or comparing a vector with the score matrix.

Referring again to FIG. 5, as represented by block 506 the matrix generator 606 processes each of the shape vectors generated at block 504 to define (e.g., update) a score matrix that provides sinus baseline information for the discrimination operation. A score matrix may be employed as a relatively efficient way of determining how frequently the components of a shape vector occurred during sinus. For example, in some embodiments the value and position of each component of the matrix comprise the row and column indices, respectively, of a score matrix entry that records the frequency with which that component value has been seen in that position. The score matrix may be calibrated on a repeated basis to ensure that it accurately reflects the characteristics of the patient's normal sinus. Several sample operations that may be performed in conjunction with the definition of a score matrix will be described in more detail in conjunction with FIG. 8.

As represented by block 802, various aspects relating to the characteristics of and the manner of constructing a score matrix may be defined when the discrimination procedure is designed, when it is initially invoked, or at some other time. As discussed below, some of these aspects relate to how information is added to the score matrix, how the growth of the matrix is controlled, how a vector is compared with the matrix, and so on. To facilitate an understanding of how a score matrix may be constructed and used, the following describes a specific example of such a construction and use. It should be appreciated, however, that the teachings herein are not limited to this specific example.

Blocks 804-808 relate to operations that may be performed to add initial entries to the score matrix. For example, in some embodiments a score matrix may be initially defined without any columns or rows. In this case, appropriate columns and rows may be defined for the score matrix as shape vector information is incorporated into the score matrix.

Accordingly, at block 804 the matrix generator 806 obtains the initial sinus-related shape vector for the score matrix. As discussed below, the initial width of the matrix may thus be set to the length (i.e., the number of entries of) the initial shape vector.

As represented by block 806, an upper bounds vector and a lower bounds vector may be defined to track the largest and smallest component values seen in each column position of the matrix up to this point in the matrix generation process. In other words, upper and lower bound values are associated with each column of the score matrix where, for a given column, the absolute value of the upper bound is set to the value of the highest row index of a non-zero entry in the column, and the absolute value of the lower bound is set to the value of the lowest row index of a non-zero entry in the column. The signs of these bounds are equal and are of opposite sign to those in neighboring columns, i.e., the signs of the bounds alternate across the matrix.

A brief example of how the upper and lower bounds of lectures may be generated follows. This example makes reference to "the parity" of a vector or a matrix. As will be discussed in more detail below, the term parity as used herein relates to whether a particular column (e.g., the first column) of a vector or a matrix is associated with a positive number or negative number. An upper bounds vector u and a lower bounds vector l are derived from shape vectors in a manner that causes them to have equal parity. Consequently, the parity of the current score matrix is equal to the parity of the upper bounds vector which is equal to the parity of the lower bounds vector. A pair $[u_k, l_k]$ is the range of shape vector component values seen thus far in position k (relative to the current score matrix). A function EXPAND(s,u,l) is defined with a shape vector $s=<s_1, s_2, \ldots, s_n>$, the upper bounds vector u, and the lower bounds vector l as inputs. The function outputs updated vectors u and l together with an integer x that measures the total expansion of the range due to the inclusion of s. The integer x relates to the operations of blocks 814-818 discussed below. The function may perform the procedure set forth in Equation 1.

Equation 1
For each component $s_k$ of s:
Replace $u_k$ with the larger of $u_k$ and $s_k$;
Replace $l_k$ with the smaller of $l_k$ and $s_k$; and Set $x=(u_1-l_1+1)(u_2-l_2+1) \ldots (u_n-l_n+1)$.

Referring again to block 806, as only the initial vector has been provided at this point of the process, the matrix generator 606 sets the upper and lower bounds for each column equal to the value of the corresponding element from the initial shape vector. Thus, in a case where the initial shape vector is: <2, −1, 3, −1, 1>, at block 806 the matrix generator 606 defines the upper bounds ("UB") and the lower bounds ("LB") for the initial matrix as shown in FIG. 9A.

As represented by block 808, the matrix generator 606 incorporates the information from the initial vector into the score matrix. In some embodiments this operation involves incrementing a count entry in the score matrix based on the absolute value of each element of the shape vector. Here, a given element of the shape vector will correspond to a given column of the score matrix. In addition, the rows of the score matrix may be defined as corresponding to a given magnitude (i.e., absolute value). FIG. 9A illustrates an example of how the information for the initial shape vector discussed above may be tallied in the score matrix M. The matrix generator 606 may then store this matrix information in an associated data memory 620.

Blocks 810-828 relate to operations that may be performed to incorporate information from additional shape vectors into the score matrix. As mentioned above, each of these shape vectors is derived from cardiac signals associated with normal sinus.

In the example of FIG. 8, the score matrix is expanded as necessary so that its width equals, but does not exceed, the width of the widest shape vector that has been "added" to the matrix. In this way, growth of the matrix may be limited, thereby facilitating the aggregation of the vector information within in relatively small range as it is expected to be given the relative similarity of successive cardiac waveforms. Through the use of such a rule, the width of the matrix will be limited due to the limited duration of a typical heartbeat. In addition, through the use of appropriate filtering, any noise that may otherwise be present at the end of the cardiac signal (which could potentially result in a very long shape vector) may be eliminated or substantially reduced. In this way, the length of each of the shape vectors, and hence the score matrix, may fall within an acceptable range.

At block 810 the matrix generator 606 obtains the next shape vector to be incorporated into the score matrix. For example, the matrix generator 606 may obtain a shape vector directly from the vector generator 604 or it may retrieve a shape vector that the vector generator 604 previously stored in a data memory.

The matrix generator 606 may then determine an appropriate alignment for the shape vector relative to the score matrix. An alignment procedure may need to be performed in cases where the next shape vector does not precisely align with the current score matrix. In such a case, the shape vector may be shifted in time in an attempt to line the vector up with the columns of the score matrix that best match the particular elements of the shape vector.

Such shifting of the shape vector may be necessary due to variations that may occur from one shape vector to the next. For example, to provide the cardiac signal for a given QRS complex, a threshold mechanism may be employed to identify the beginning of the complex. However, due to variations in the cardiac signals (e.g., variations in amplitude or noise levels), a given signal may be truncated on the left or right. Thus, different shape vectors may not have the same length and their shape components that correspond to the same part of the QRS complex may appear in different positions relative to the start of the vector. In other words, the beginning of a given acquired cardiac signal may relate to a different time in the QRS complex than the beginning of another acquired cardiac signal. Consequently, corresponding elements (e.g., the first element) of each of the shape vectors may not all correspond to the same point in time (e.g., the beginning) with respect to the actual QRS complex. Alignment may therefore be employed in an attempt to properly align the timing of the vector obtained at block 810 with the vector information that has already been incorporated into the score matrix. FIGS. 10-13 describe four different alignment scenarios.

Figure 10:
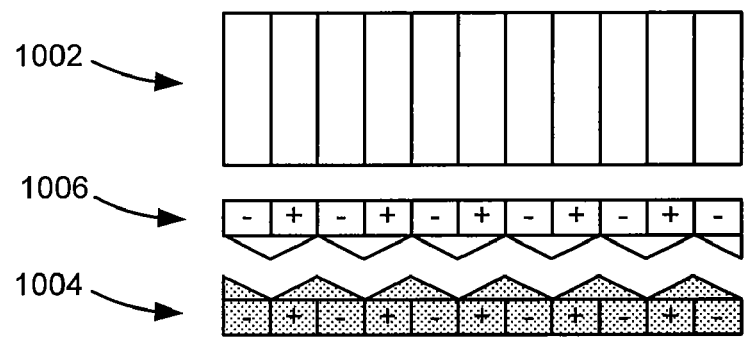
FIG. 10 is a simplified diagram illustrating alignment of representations of a score matrix and a shape vector.

FIG. 10 illustrates a simplified example of a score matrix 1002 and a shape vector 1004. For convenience, the rows of the matrix 1002 are not shown in FIG. 10.

The structure 1006 in FIG. 10 is simply for illustration purposes. Specifically, the structure 1006 represents that the matrix 1002 may be considered to have a particular parity, with respect to whether the first column in the score matrix is associated with a positive number or negative number. For example, in FIG. 9A the first column of the matrix M is associated with positive numbers (since the first element of the initial shape vector was positive). Thus, the score matrix inherits its polarity from the polarity of last shape vector that caused an increase in the size of the score matrix.

For convenience, a matrix or vector may be referred to herein as having even parity if its even-numbered components are positive and having odd parity if its odd-numbered components are positive, where the leftmost column is numbered column zero. Thus, a vector or matrix having a first column that is associated with a negative number (e.g., as in FIG. 9A) may be referred to herein as having odd parity.

The serrated edges of the shape vector 1004 and the structure 1006 also are simply for illustration purposes. Specifically, the serrated edges provide a visual clue to indicate that positive elements of the shape vector 1004 should be aligned with positive columns of the score matrix 1002. From this representation, it may be observed that the use of a shape vector with alternating sign elements serves to reduce the computations needed to update the score matrix 1002 since the shape vector 1004 needs to shift by twos to properly align with the score matrix 1002. In other words, essentially half as many potential alignment cases may need to be tested to determine the proper alignment between the score matrix and the shape vector in cases where there not exact alignment (discussed below).

In the example of FIG. 10 the score matrix 1002 and the shape vector 1004 are in "exact alignment." That is, the length of the shape vector 1004 is the same as the width of the score matrix 1002 and the two structures have identical parity. In such a case, no other alignments are attempted because any other alignment would increase the size of the score matrix 1002.

Figure 11A:
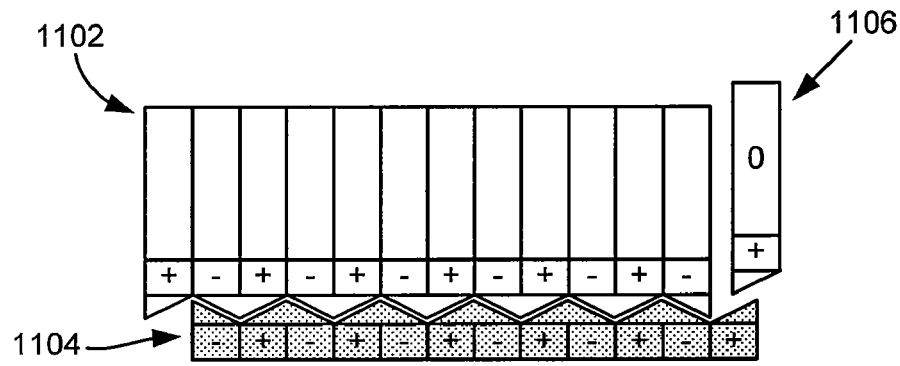
FIGS. 11A and 11B, depicts in a simplified manner different alignments of representations of a score matrix and a shape vector.
Figure 11B:
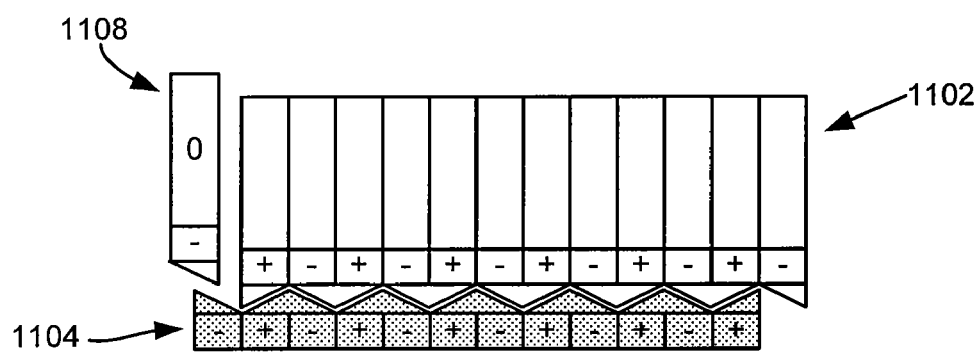

FIG. 11 illustrates a case, designated "parity alignment" for convenience, where the width of a score matrix 1102 is the same as the length of a shape vector 1104, but where the two structures have different polarities. Here, there are two parity alignments of the score matrix 1102 and the shape vector 1104 that are allowed as shown in FIGS. 11A and 11B. In other words, to constrain the growth of the score matrix 1102 the shape vector 1104 may not be allowed to protrude beyond the ends of the score matrix 1102 by more than one column. In practice, a rule such as this may not adversely affect the matrix generation process to a significant degree since, given the similar sizes of the score matrix 1102 and the shape vector, the information contained in them is likely to be only slightly shifted with respect to one another, if at all.

For "parity alignment" the width of the score matrix is thus increased by a single column to accommodate a corresponding end element of the shape vector 1104. Specifically, in FIG. 11A a zero column 1106 is added to the end of the score matrix 1102 while in FIG. 11B a zero column 1108 is added to the beginning of the score matrix 1102. As will be discussed below, the matrix generator 606 may be configured to perform alignment operations to determine whether the alignment of FIG. 11A or the alignment of FIG. 11B is to be used to update the matrix 1102 based on the contents of the shape vector 1104.

Figure 12:
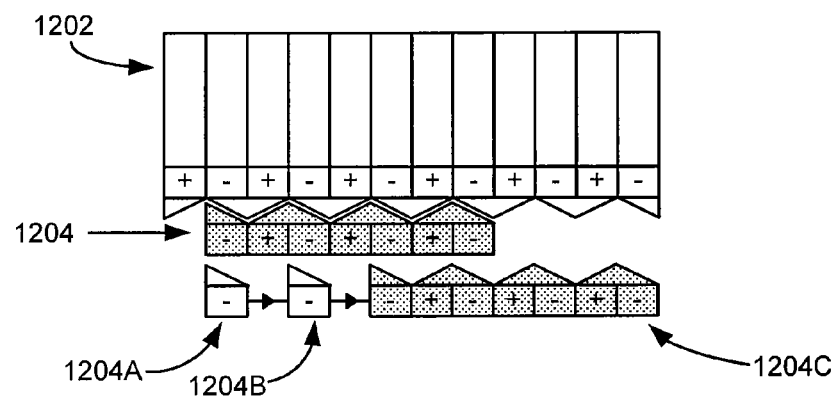
FIG. 12 is a simplified diagram illustrating alignments of representations of a shape vector with a representation of a larger score matrix.

FIG. 12 illustrates an example of a scenario, designated "interior alignment" for convenience, where score matrix 1202 is wider than the shape vector 1204. In this case, the matrix generator 606 checks all of the allowed alignments of the shape vector with the score matrix to identify the best alignment. Here, it may be seen that the shape vector may be aligned in three different ways as indicated by the positions 1204A, 1204B, and 1204C. Again, in conjunction with the sample matrix definition set forth above, the shape vector 1204 is not allowed to protrude beyond the ends of the score matrix 1202. One basis for this rule in this case is that the likely reason for the shape vector 1204 being shorter than the score matrix 1202 is that information is missing at either end of the shape vector 1204. Moreover, it is unlikely that the most useful information in the shape vector 1204 is at the end of the shape vector 1204. Hence, allowing the vector 1204 to extend beyond the matrix 1202 typically would not result in good alignment.

Figure 13:
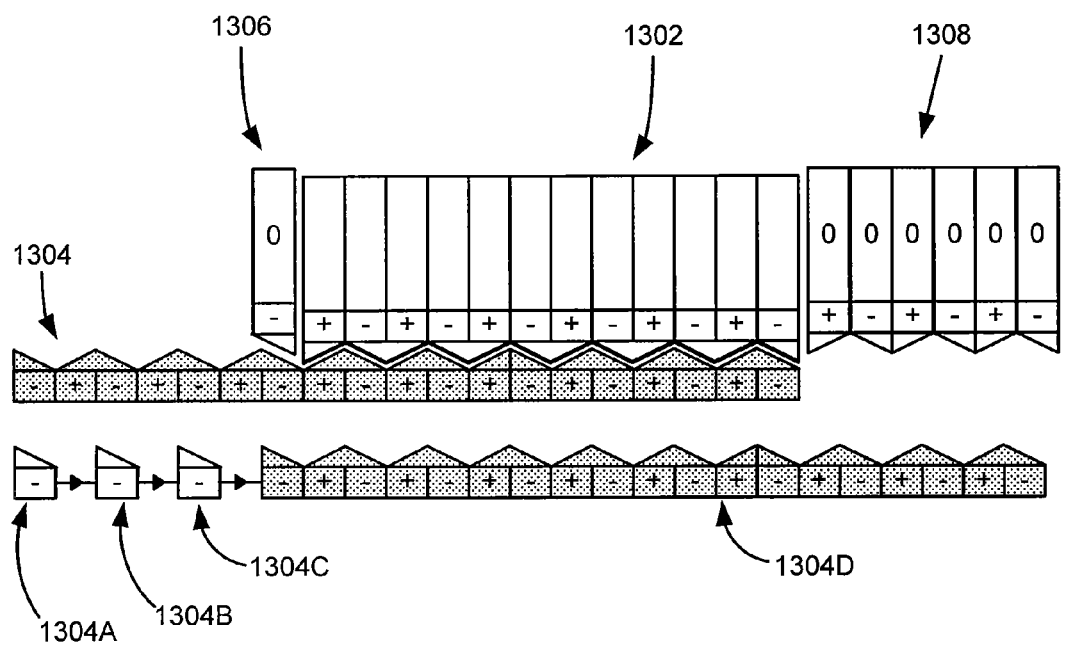
FIG. 13 is a simplified diagram illustrating alignments of representations of a shape vector with a representation of a smaller score matrix.

FIG. 13 illustrates an example of a scenario, designated "exterior alignment" for convenience, where score matrix 1302 is narrower than shape vector 1304. In this case, the width of the score matrix 1302 will be expanded to match the larger width of the shape vector 1304. However, the score matrix 1302 is constrained to not protrude beyond the ends of the shape vector 1304. Consequently, the four allowable alignments of the shape vector 1304 with the score matrix 1302 are indicated by the positions 1304A, 1304B, 1304C, and 1304D of the shape vector 1304. FIG. 13 also illustrates that once an appropriate alignment is found, the score matrix 1304 is augmented with zero columns (e.g., columns 1306 and 1308) to match the size of the shape vector 1304

Referring again to FIG. 8, the operations of blocks 812-822 may be performed in the event there is more than one potential alignment. That is, if there is exact alignment as in FIG. 10, these operations are not performed. Conversely, if there are multiple allowable alignments as in the examples of FIGS. 11-13, the matrix generator 606 performs the operations of blocks 812-822.

In some embodiments a desired alignment is defined as one that results in the smallest increase in the range between the bounds vectors. As mentioned above, whenever a shape vector is added to the score matrix, the upper and lower bonds may be adjusted as necessary to account for the new vector. Thus, as described in Equation 1, if for a given column the corresponding element of the new vector is of greater magnitude than the upper bounds, the upper bounds value for that column is set to the value of that element. A similar rule is followed for the lower bounds.

At blocks 812-820 the matrix generator 606 may thus calculate, for each prospective alignment, the difference between each element of the shape vector and the upper and lower bounds for the corresponding column. Accordingly, at block 812 the matrix generator 606 selects one of the prospective alignments for the shape vector.

For illustration purposes a simplified example of an alignment decision operation follows. It will be assumed that the following shape vector is to be added to the score matrix of FIG. 9A: <3, −2, 2>. According to the rules discussed above (e.g., in conjunction with FIG. 8), the two allowable alignments are represented by vectors 904A and 904B in FIG. 9B. The absolute difference between vector 904A and the corresponding columns of the upper and lower bounds (i.e., the extent to which any given element of the shape vector fall outside the current range of the upper and lower bounds) is |3−2|=1; |−2−−1|=1; |2−3|=1. Thus, the corresponding difference vector calculated at block 814 for vector 904A is: <1, 1, 1>.

Referring to blocks 816 and 818, in the current example the determination as to which of the alignments results in smallest growth of the bounds vectors is determined by comparing an effective hyper-volume associated with each difference vector. In Equation 1, this operation relates to the calculation of the integer x. Hence, to prevent multiplication by zero (e.g., as illustrated by the difference vector for the vector 904B discussed below), the value of each element of the difference vectors are incremented by one (block 816) as shown in Equation 1. Hence, the difference vector for vector 904A is modified to: <2, 2, 2>.

At block 818 the matrix generator 606 computes the hyper-volume (e.g., the integer x) for the difference vector. Thus, for the above example the volume is: 2×2×2=8.

As represented by block 820, the operations of blocks 812-818 are repeated for each prospective alignment. Thus, at block 812 the matrix generator 606 selects the alignment of vector 904B. The absolute difference between vector 904B and the corresponding columns of the upper and lower bounds is: |3−3|=0; |−2−−1|=1; |2−1|=1. Thus, the difference vector calculated at block 814 for vector 904B is: <0, 1, 1>. This difference vector is then adjusted at block 816 to: <1, 2, 2>. The hyper-volume computed at block 818 is therefore: 1×2×2=4.

After the matrix generator 606 has computed the hyper-volumes for all of the prospective alignments, the procedure passes to block 822 where the matrix generator 606 selects the alignment associated with the smallest hyper-volume. Thus, in the example of FIG. 9B, the alignment of vector 904B is selected.

At block 824 the matrix generator 606 adjusts the upper and lower bounds as necessary according to Equation 1. The new upper and lower bounds resulting from the selection of vector 904B are shown in FIG. 9C.

At block 826 the matrix generator 606 updates the matrix to include information associated with the vector 904B. In the matrix M' of FIG. 9C, the entry for the magnitude "3" row in the third column has been increased by one. In addition, entries for magnitude "2" have been added to the fourth and fifth columns. It should thus be appreciated that the score matrix essentially comprises a frequency chart that indicates the frequency with which certain components (e.g., inflection point-related characteristics) occur at a given relative position in the cardiac signal.

The example of FIG. 9 illustrates a case where the size of the matrix M did not increase as a result of the incorporation of the information from the shape vector 904B. In the event the addition of a vector does result in the addition of one or more columns to the score matrix, the upper and lower bounds in the matrix may be adjusted in a similar manner as discussed above. For example, the upper and lower bounds for the new column will be set to the magnitude of the corresponding element of the shape vector. In addition, a tally will be provided in the new column of the matrix in a row that corresponds to the magnitude of the corresponding element of the shape vector.

Also, it should be appreciated that additional rows may be added to the score matrix in the event a new shape vector includes a magnitude that is not presently included the score matrix. Referring again to the example of FIG. 9C, if the new shape vector includes an element having a magnitude of four, a new row corresponding to a magnitude of four will be appended to the bottom of the score matrix M'.

As represented by block 828 the operations of blocks 810-826 are repeated as necessary for each sinus-related shape vector that is to be incorporated into the score matrix. As mentioned previously, this matrix calibration process may be repeated over time to ensure that the score matrix accurately represents cardiac signals during sinus.

The above operations may be described in terms of a function that is called to update the score matrix. Here, somewhat different procedures may be followed depending on whether the score matrix and the shape vector to be added to the score matrix are in exact alignment, parity alignment, interior alignment, or exterior alignment. Each of these cases will be discussed in turn.

For the case of exact alignment, a function ACCUMULATE(s,M) is defined with a shape vector $s=<s_1, s_2, \ldots s_n>$, and a matrix M as inputs, where the matrix M has n columns. The function outputs a matrix M that also has n columns, but may have extra rows. The function may then perform the procedure set forth in Equation 2.

Equation 2

Let $M_{i,j}$ denote the cell in the $i^{th}$ row and the $j^{th}$ column of M.

For each component $s_j$ of s:
Let $i=|s_j|$, the absolute value of $s_j$;
Pad M with zero rows as necessary until M has at least i rows;
Increment $M_{i,j}$ by 1.

Here, the structures M and s that are input to this iteration all are ready of the correct form. Accordingly, the exact alignment procedure first invokes EXPAND(s,u,l) to update the upper and lower bounds vectors, then invokes ACCUMULATE(s,M) to update the score matrix, and then returns.

For the case of parity alignment, as mentioned above the better of two possible alignments that have matching parity is selected. In one alignment the first component of s is aligned with the second column of M while in the other alignment the second component of s is aligned with the first column of M. In either case some part of the vector will line up with part of the upper and lower bounds vectors. The alignment chosen is that which has a smaller total expansion value and is computed by EXPAND(s,u,l) on the appropriate vectors. This also updates the upper and lower bounds vectors associated with the score matrix. The score matrix is then padded with a zero column on the left or right as appropriate and the column on the opposite end is excluded to produce a sub-matrix M' of M. The function ACCUMULATE(s,M) is invoked to update M, then the function returns.

For the case of interior alignment, the desired alignment may be found by sliding the shape vector within the matrix up to the position that minimizes the expansion value. Accordingly, EXPAND(s,u',l') is called repeatedly with u' and l' being the sub-vectors of u and l corresponding to s. Finally, the function ACCUMULATE(s,M') is invoked to update M, where M' is the sub-matrix of M that lines up with s.

For the case of exterior alignment, the desired alignment may be found by sliding the matrix within the vector up to the position that minimizes the expansion value. Thus, EXPAND (s',u,l) is called repeatedly with s' being the sub-vector of s that lines up with M. Once this alignment has been found, the score matrix is padded on the left and right with zero columns until it lines up with s, in particular so that the width of the score matrix matches the length of s. After the bounds vectors are updated, the function invokes ACCUMULATE(s,M) to update M and returns.

Referring again to FIG. 8, as represented by block 830 the matrix generator 606 (or the discriminator 608) may optionally identify a core component of the matrix. Due to the truncation of the shape vectors and the consequent variance in the lengths of the shape vectors, the column totals in the score matrix tend to decrease toward the ends of the matrix. In other words, the columns toward the center of the score matrix tend to have frequency information that more accurately represents the cardiac signals during sinus. Consequently, the core of the score matrix contains information that may be most useful in determining how best to align candidate shape vectors with the score matrix during the discrimination process.

In view of the above, the core of the score matrix is defined as a sub-matrix that includes those columns that have the highest total scores. Here, the score of a given column may be defined as the sum of each of the entries in that column. As an example, the total scores for each of the five columns in FIG. 9C are 1; 1; 2; 1+1=2; and 1+1=2, respectively.

Figure 15:
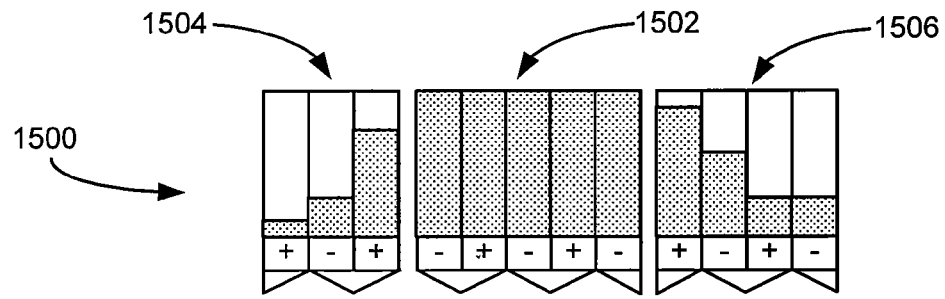
FIG. 15 is a simplified diagram illustrating a representation of a core of a score matrix.

FIG. 15 illustrates an example of a core matrix 1502 of a matrix 1500. Here, the shading in each of the columns represents the magnitude of the count for that column. Thus, in the example of FIG. 15 the columns selected for the core matrix 1502 have higher count values than outlying portions 1504 and 1506 of the matrix 1500.

In cases where there is a good degree of similarity between the shape vectors being added to the matrix, the number of entries for each column in the core matrix may equal the total number of shape vectors that have been added to the matrix. As an example, if the score matrix is generated using nine shape vectors, the summation of all of the entries in a given column of the core may, at most, be equal to nine.

Referring again to FIG. 5, the use of the score matrix during discrimination operations will now be treated in more detail. As represented by block 508, at some point in time a tachycardia detector 622 (FIG. 6) may identify a potential tachycardia. In a typical implementation this operation may involve analyzing the IEGM signals that are continually generated by the cardiac acquisition circuit 602 as discussed above. In addition, in some embodiments the detector 622 may identify tachycardia by monitoring one or more physiological parameters, performing threshold detection, performing morphology discrimination, performing some other operation, or performing some combination of two or more of these operations.

As represented by block 510, the discrimination system 600 may acquire cardiac signals that correspond to a time period when tachycardia was indicated. This may involve, for example, using the IEGM signals that were used to generate the indication of tachycardia at block 508.

At block 512 the vector generator 604 generates a set of shape vectors based on the cardiac signals collected a block 510. These vector generation operations may be similar to the operations of FIG. 7 discussed above.

At block 514 the discriminator 608 scores the shape vectors generated at block 512 using the score matrix. At block 516, in the event the comparison at block 514 indicates that enough of the cardiac signals associated with the tachycardia are sufficiently similar to sinus signals, the device 600 may classify the tachycardia as super-ventricular (block 518). This classification, in conjunction with one or more other therapy discrimination operations, may lead to the administration of appropriate therapy for super-ventricular tachycardia. On the other hand, if not enough of these cardiac signals are sufficiently similar to sinus signals, the device 600 may classify the tachycardia as ventricular (block 520). This classification, in conjunction with one or more other therapy discrimination operations, may thus lead to the administration of appropriate therapy for ventricular tachycardia.

In some embodiments the operations of block 514 may involve scoring each of the vectors generated at block 512 against the score matrix. Briefly, this operation may involve collecting and scoring several QRS complexes, and comparing the sum of these scores with a threshold that is based on the score matrix. Several sample operations that may be performed in conjunction with the scoring of shape vectors will be described in more detail in conjunction with FIG. 14.

The operations of blocks 1402-1412 relate to generating scores for each of the tachycardia-related shape vectors under consideration. In practice, the shape vectors associated with tachycardia may vary in length and parity in a similar manner as discussed above. Consequently, these operations involve determining the best alignment for each shape vector relative to the score matrix. At block 1402 the discriminator 608 obtains one of the shape vectors to be processed. At block 1404 the discriminator 608 identifies a valid alignment for the shape vector with respect to the score matrix. At block 1406 the discriminator 608 scores the selected shape vector. As represented by block 1408, the operations of blocks 1404 and 1406 are repeated to generate scores for all of the prospective alignments for the selected vector.

Figure 16:
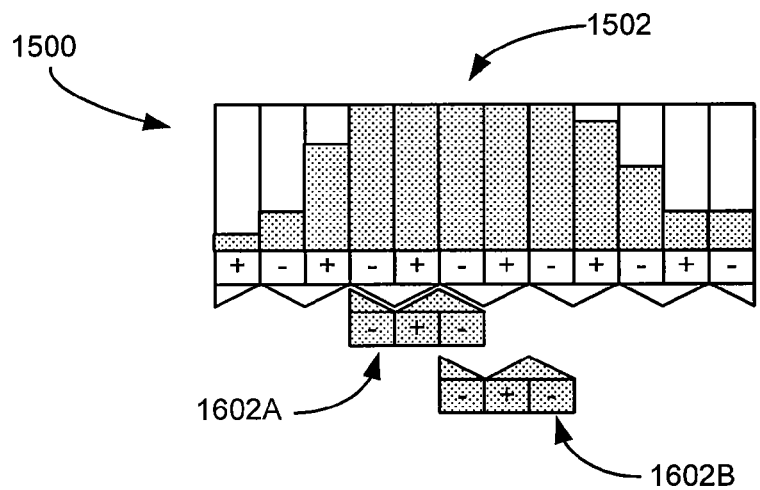
FIG. 16 is a simplified diagram illustrating alignments of representations of a shape vector with a representation of a larger core of a score matrix.
Figure 17:
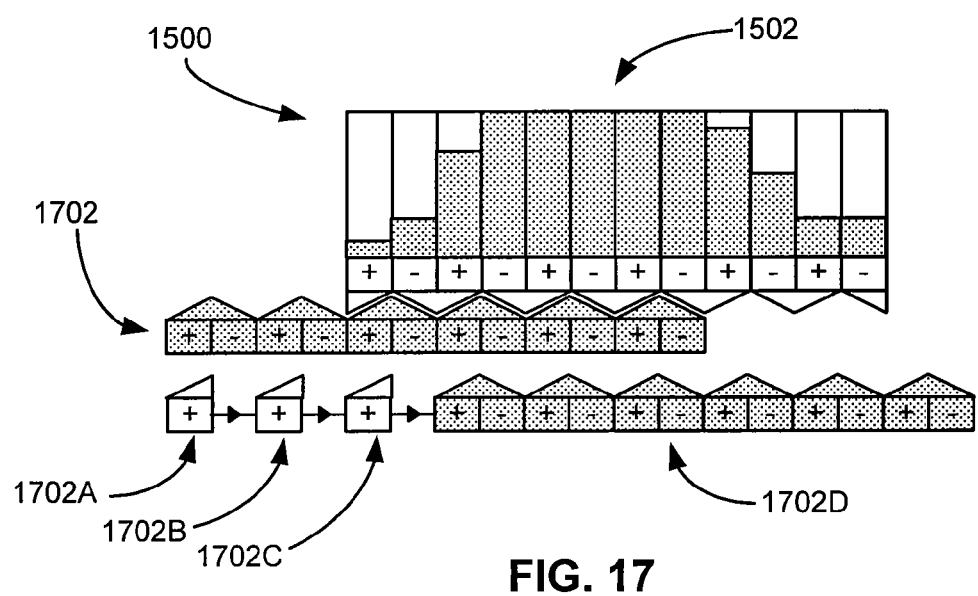
FIG. 17 is a simplified diagram illustrating alignments of representations of a shape vector with a representation of a smaller core of a score matrix.

FIGS. 16 and 17 illustrate examples of potential alignments of shape vectors with the core 1502 of the matrix 1500. In the example of FIG. 16 the shape vector 1602 is narrower than the core 1502. In this case, all alignments with the shape vector 1602 interior to the core 1502 will be scored and the highest score retained. In this case, two potential alignments as represented by the vectors 1602A and 1602B are tested.

In the example of FIG. 17 the shape vector 1702 is wider than the core 1502. In this case, all alignments with the shape vector 1702 exterior to the core will be scored and the highest score retained. Here, four potential alignments as represented by the vectors 1702A-1702D are tested.

At block 1410, the discriminator 608 identifies the best alignment from all of the potential alignments for a given vector. Here, the best alignment may be defined as the alignment that has the highest score and is intended to provide the best match between the individual elements of the shape vector and corresponding columns of the core of the score matrix.

In some embodiments a function, named ALIGNED_SCORE(s,N) in this example, may be used to score the shape vectors. Here, the input to the function is a shape vector $s = <s_1, s_2, \ldots s_n>$ and a matrix N, wherein the matrix N has n columns, and where the parity of s is equal to the parity of N. The function outputs an integer m that scores the current alignment of with N. The function may then perform the procedure set forth in Equation 3.

Equation 3
Set m=0
For each component $s_j$ of s:
Let $i=|s_j|$, the absolute value of $s_j$;
Add $N_{i,j}$ to m.

For the case when the length of the shape vector is less than the width of the core (e.g., as in FIG. 16) the best alignment for the shape vector is found by sliding the shape vector within the core to identify the position that maximizes m=ALIGNED_SCORE(s,N). Hence, N is the sub-matrix of the core (e.g., three of the columns of the core 1502 in FIG. 16) that lines up with the shape vector s (e.g., vector 1602). The maximum value m is the score of the shape vector.

For the case where the shape vector is as wide as or wider than the core the best alignment is found by sliding the core within the shape vector to identify the position that maximizes M=ALIGNED_SCORE(v',M'), where v' and M' are the portions of the shape vector V and the matrix M', respectively, that lineup. For example, for the alignment associated with the shape vector 1702D in FIG. 17, v' comprises the 10 leftmost elements of the shape vector 1702D and M' comprises the 10 rightmost elements of the score matrix 1500.

The example where the shape vector is as wide as or wider than the core includes two sub-cases. In the first sub-case the width of the matrix is greater than or equal to the length of the shape vector. Here, the maximum value m is the score of the shape vector.

In the second sub-case the width of the matrix is less than the length of the shape vector. Here, it is likely that there are noise artifacts within the shape vector that have artificially inflated its score. In such a case, the score may be penalized by, for example, replacing m with m÷(length(s)−width(M)), where M is the score matrix.

Figure 18:
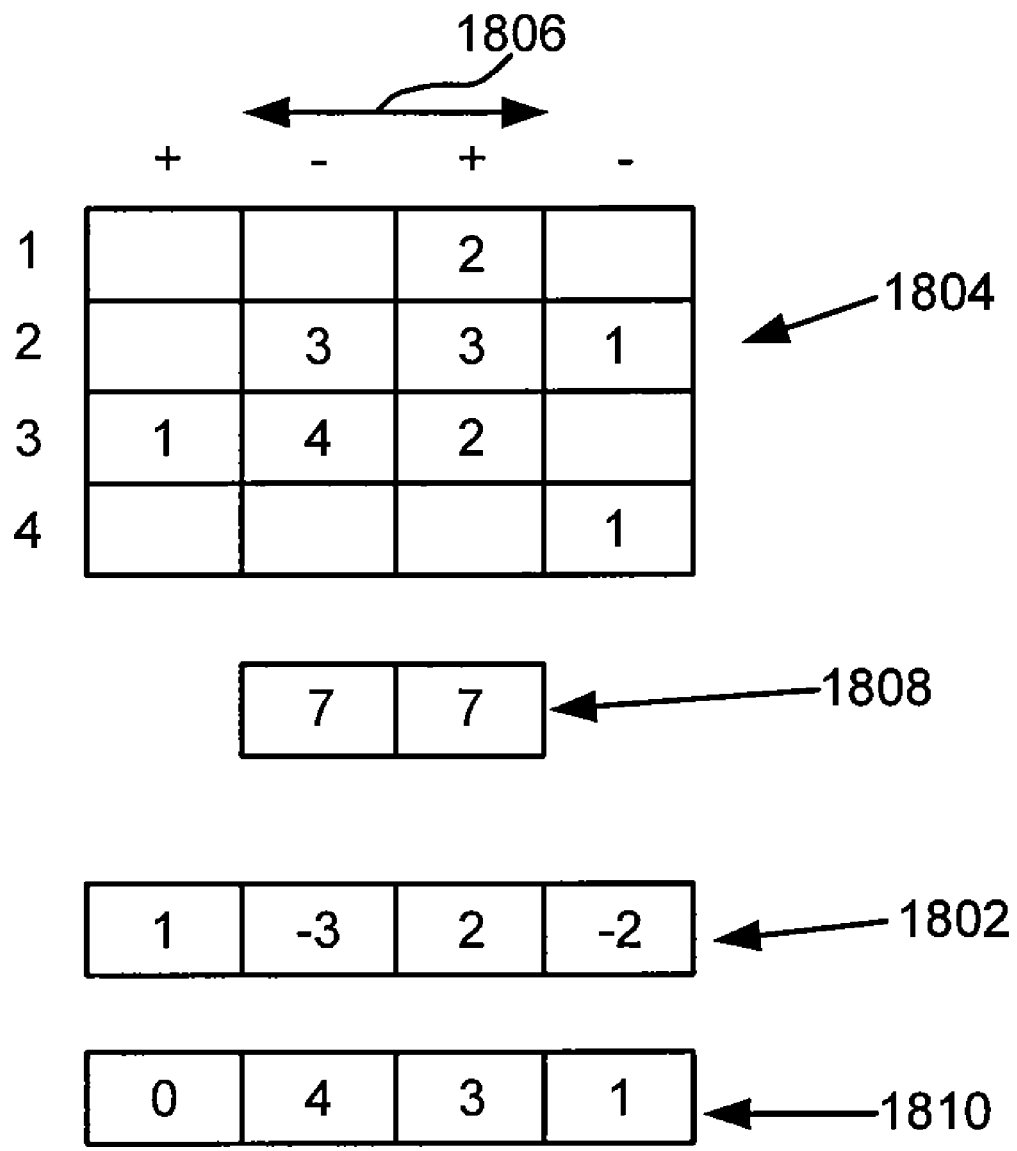
FIG. 18 is a simplified diagram illustrating scoring of a shape vector.

FIG. 18 illustrates a sample scoring of a vector 1802 with respect to a matrix 1804 having a core 1806. The polarity of the matrix 1804 is indicated by the plus and minus signs immediately above the matrix 1804. Also, the row of the matrix corresponding to a magnitude of zero is not shown since there will be no entries in this row. It should be appreciated, however, that the zero row may still be employed in a score matrix to facilitate accessing the entries of the matrix through the use of an index-based technique.

The vector 1808 illustrates that the totals for the two middle columns of the matrix 1804 are higher than the totals of the two outer columns. Hence, these two middle columns have been selected as the core 1806 of the matrix 1804.

The vector 1802 is defined as: <1, −3, 2, −2>. Given the parity of the core 1806 (as represented by the corresponding minus and plus signs), the only valid alignment of the vector 1802 is the alignment depicted in FIG. 18. In other words, under the set of rules defined above, this is the only alignment where the parities of the core 1806 and the shape vector 1802 are equal and where the core 1806 does not extend beyond the shape vector 1802.

The vector 1810 illustrates the corresponding counts (e.g., weights) for each of the elements of the vector 1802. Specifically, for the first element of the vector 1802, the first column of the matrix 1804 does not include any entries associated with a magnitude of "1." For the second element of the vector 1802, the second column of the matrix 1804 includes four entries associated with a magnitude of "3." The remaining entries for the vector 1810 are calculated in a similar manner. Accordingly, the total score for this alignment of the matrix 1802 is the sum of the values in the vector 1810, namely "8."

Once all of the shape vectors have been scored at blocks 1402-1412, the discriminator 608 compares the scores to one or more corresponding baselines. For example, at block 1414 the discriminator 608 may sum all of the scores that were generated for the different tachycardia-related shape vectors and saved at block 1410. At block 1416 the discriminator compares this sum to a baseline that is based on the score matrix to determine, for example, the degree of similarity between the shape vectors and the matrix.

In some embodiments the baseline is based on the maximum possible score that may be obtained from the score matrix. Here, a maximum score $S_{max}$ may be defined that comprises the sum of the largest values in each column of the score matrix. Consequently, the maximum total score from a tachycardia episode where n shape vectors have been provided for the discrimination operation is $nS_{max}$. Referring to the example of FIG. 18, $S_{max}$ is equal to: 1+4+3+1=9. Hence, in a case where 16 shape vectors are processed during the discrimination operation, $nS_{max}$ is equal to 9×16=144.

In some implementations the baseline (e.g., a threshold) is defined as a percentage of this maximum total score. For example, if $S_1, S_2, \ldots, S_n$ are the scores obtained during the tachycardia episode (e.g., generated and saved at block 1410), then the match ratio is $(S_1+S_2+ \ldots +S_n)\div nS_{max}$. Here, it should be appreciated that the scoring baseline may be reset each time the score matrix is recalibrated.

At block 1418, any result less than the threshold (e.g., 0.5 or 50%) may be declared to be associated with a morphology distinct from sinus while any result that is equal to or above the threshold may be declared to be associated with a morphology that is indistinguishable from sinus. It should be appreciated that other tests may be employed here and that such tests may utilize, for example, a different baseline, different baseline tests, a different number of baselines, and so on.

Blocks 1420 and 1422 relate to operations that may be performed in the event the composite score is, for example, below the baseline at block 1418. At block 1420 a tachycardia indication generator 624 (FIG. 6) generates an indication of ventricular tachycardia. At block 1422, based on this indication a tachycardia therapy module 626 provides or otherwise facilitates the application of appropriate therapy to the patient (e.g., a shock and/or medication).

Blocks 1424 and 1426 to relate to operations that may be performed in the event the composite score is, for example, equal to or above the baseline at block 1418. In this case, at block 1424 the tachycardia indication generator 624 generates an indication of super-ventricular tachycardia. In addition, at block 1422 the tachycardia therapy module 626 provides or otherwise facilitates the application of appropriate therapy to the patient (e.g., pacing and/or medication).

In some embodiments the indication generated by the tachycardia indication generator 624 may comprise a warning signal. For example, the tachycardia indication generator 624 may generate an indication to provide a warning to the patient, a physician, some other person, or some other device. Thus, in some implementations an indication may be sent to an external apparatus that then forwards the indication or generates an otherwise appropriate signal.

As mentioned above, the tachycardia therapy module 626 may cause treatment to be applied to a patient or result in a modification of a current treatment for the patient. For example, the tachycardia therapy module 626 may comprise or be associated with implanted leads, signal generators, and implanted drug delivery apparatuses, to provide or otherwise facilitate the application of therapy (e.g., a shock, pacing, or drug delivery) to the patient in response to the tachycardia indication.

As represented by block 1428 in FIG. 14, the morphology discrimination system may then continue monitoring cardiac signals, updating the score matrix, classifying cardiac episodes, and performing other operations as taught herein.

Exemplary Cardiac Device

As mentioned above, the discrimination techniques taught herein may be implemented in an implantable device. The following description sets forth an exemplary implantable cardiac device (e.g., a stimulation device such as an implantable cardioverter defibrillator, a pacemaker, etc.) that is capable of being used in connection with the various embodiments that are described herein. It is to be appreciated and understood that other cardiac devices, including those that are not necessarily implantable, may be used and that the description below is given, in its specific context, to assist the reader in understanding, with more clarity, the embodiments described herein.

Figure 19:
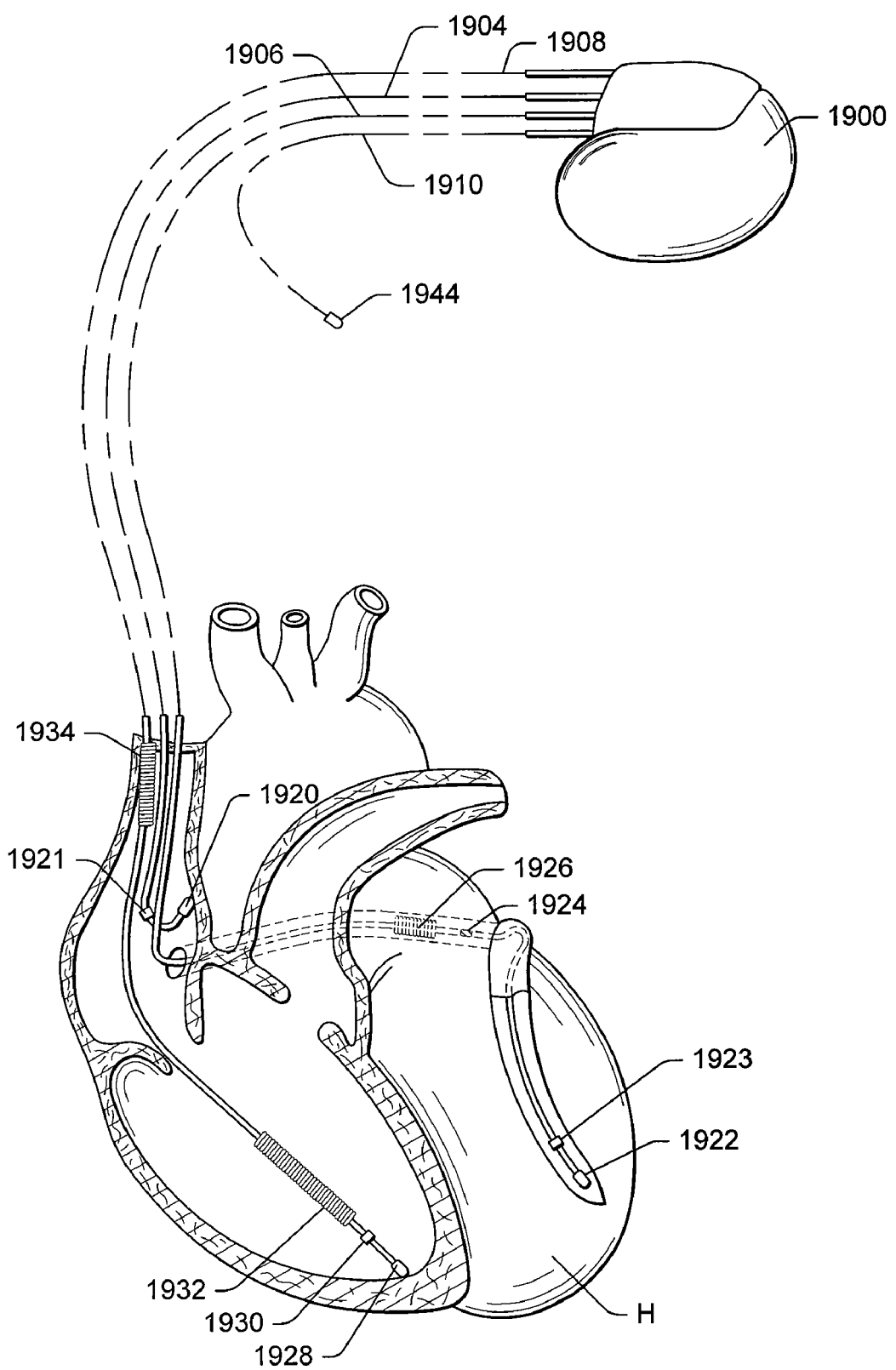
FIG. 19 is a simplified diagram of an embodiment of an implantable stimulation device in electrical communication with one or more leads implanted in a patient's heart for sensing conditions in the patient, delivering therapy to the patient, or providing some combination thereof.

FIG. 19 shows an exemplary implantable cardiac device 1900 in electrical communication with a patient's heart H by way of three leads 1904, 1906, and 1908, suitable for delivering multi-chamber stimulation and shock therapy. To sense atrial cardiac signals and to provide right atrial chamber stimulation therapy, the device 1900 is coupled to an implantable right atrial lead 1904 having, for example, an atrial tip electrode 1920, which typically is implanted in the patient's right atrial appendage or septum. FIG. 19 also shows the right atrial lead 1904 as having an optional atrial ring electrode 1921.

To sense left atrial and ventricular cardiac signals and to provide left chamber pacing therapy, the device 1900 is coupled to a coronary sinus lead 1906 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 1906 is designed to receive atrial and ventricular cardiac signals and to deliver left ventricular pacing therapy using, for example, a left ventricular tip electrode 1922 and, optionally, a left ventricular ring electrode 1923; provide left atrial pacing therapy using, for example, a left atrial ring electrode 1924; and provide shocking therapy using, for example, a left atrial coil electrode 1926 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 1900 is also shown in electrical communication with the patient's heart H by way of an implantable right ventricular lead 1908 having, in this implementation, a right ventricular tip electrode 1928, a right ventricular ring electrode 1930, a right ventricular (RV) coil electrode 1932 (or other electrode capable of delivering a shock), and a superior vena cava (SVC) coil electrode 1934 (or other electrode capable of delivering a shock). Typically, the right ventricular lead 1908 is transvenously inserted into the heart H to place the right ventricular tip electrode 1928 in the right ventricular apex so that the RV coil electrode 1932 will be positioned in the right ventricle and the SVC coil electrode 1934 will be positioned in the superior vena cava. Accordingly, the right ventricular lead 1908 is capable of sensing or receiving cardiac signals, and delivering stimulation in the form of pacing and shock therapy to the right ventricle.

The device 1900 is also shown in electrical communication with a lead 1910 including one or more components 1944 such as a physiologic sensor. The component 1944 may be positioned in, near or remote from the heart.

It should be appreciated that the device 1900 may connect to leads other than those specifically shown. In addition, the leads connected to the device 1900 may include components other than those specifically shown. For example, a lead may include other types of electrodes, sensors or devices that serve to otherwise interact with a patient or the surroundings.

Figure 20:
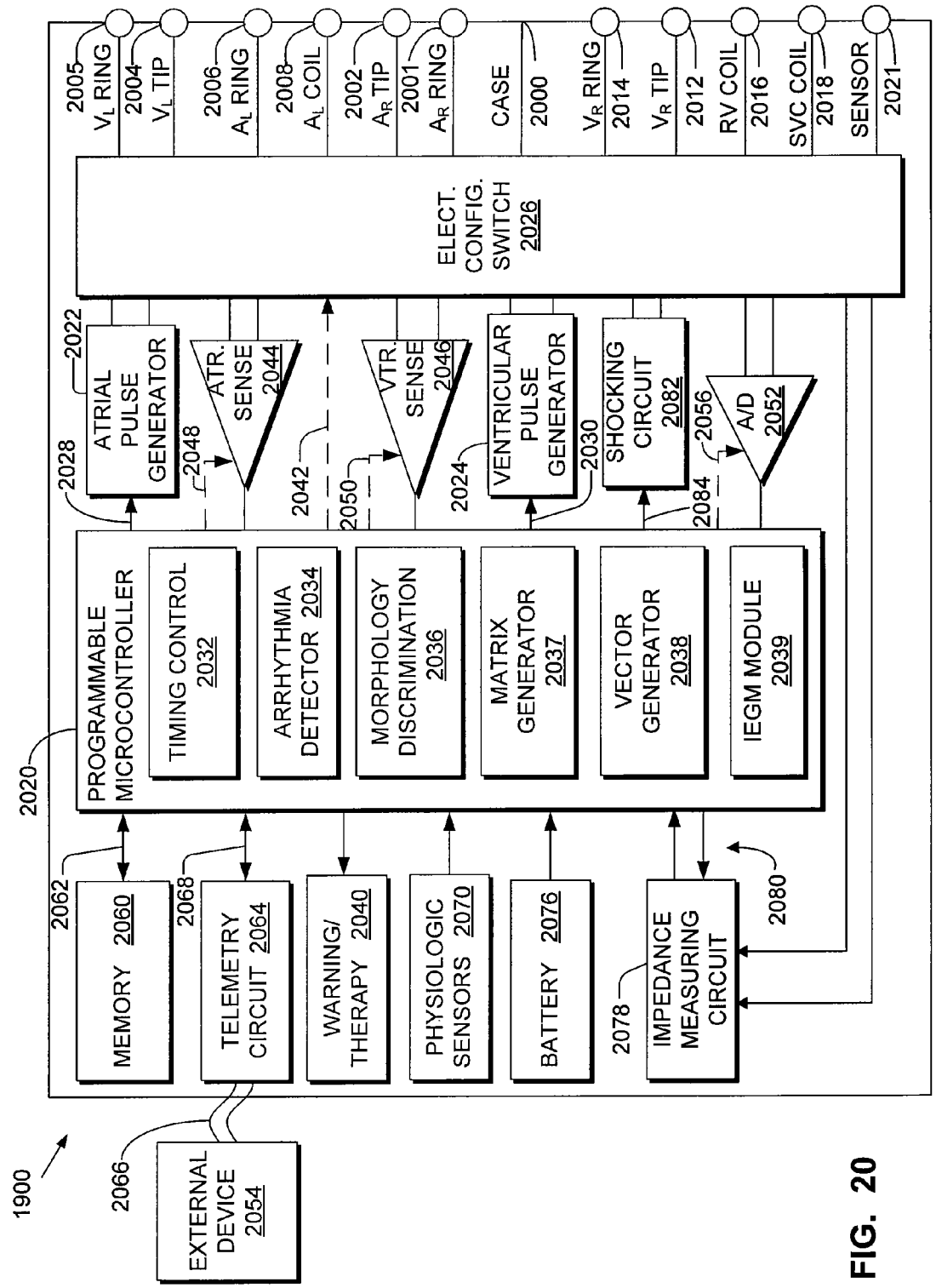
FIG. 20 is a simplified functional block diagram of an embodiment of an implantable cardiac device, illustrating basic elements that may be configured to sense conditions in the patient, deliver therapy to the patient, or provide some combination thereof.

FIG. 20 depicts an exemplary, simplified block diagram illustrating sample components of the device 1900. The device 1900 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 2000 for the device 1900 is often referred to as the "can", "case" or "case electrode", and may be programmably selected to act as the return electrode for all "unipolar" modes. The housing 2000 may further be used as a return electrode alone or in combination with one or more of the coil electrodes 1926, 1932 and 1934 for shocking purposes. Housing 2000 further includes a connector (not shown) having a plurality of terminals 2001, 2002, 2004, 2005, 2006, 2008, 2012, 2014, 2016 and 2018 (shown schematically and, for convenience, the names of the electrodes to which they are connected are shown next to the terminals). The connector may be configured to include various other terminals depending on the requirements of a given application (e.g., a terminal 2021 coupled to a sensor or some other component).

To achieve right atrial sensing and pacing, the connector includes, for example, a right atrial tip terminal (AR TIP) 2002 adapted for connection to the right atrial tip electrode 1920. A right atrial ring terminal (AR RING) 2001 may also be included and adapted for connection to the right atrial ring electrode 1921. To achieve left chamber sensing, pacing, and shocking, the connector includes, for example, a left ventricular tip terminal (VL TIP) 2004, a left ventricular ring terminal (VL RING) 2005, a left atrial ring terminal (AL RING) 2006, and a left atrial shocking terminal (AL COIL) 2008, which are adapted for connection to the left ventricular tip electrode 1922, the left ventricular ring electrode 1923, the left atrial ring electrode 1924, and the left atrial coil electrode 1926, respectively.

To support right chamber sensing, pacing, and shocking, the connector further includes a right ventricular tip terminal (VR TIP) 2012, a right ventricular ring terminal (VR RING) 2014, a right ventricular shocking terminal (RV COIL) 2016, and a superior vena cava shocking terminal (SVC COIL) 2018, which are adapted for connection to the right ventricular tip electrode 1928, the right ventricular ring electrode 1930, the RV coil electrode 1932, and the SVC coil electrode 1934, respectively.

At the core of the device 1900 is a programmable microcontroller 2020 that controls the various modes of stimulation therapy. As is well known in the art, microcontroller 2020 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 2020 includes the ability to process or monitor input signals (data or information) as controlled by a program code stored in a designated block of memory. The type of microcontroller is not critical to the described implementations. Rather, any suitable microcontroller 2020 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 20 also shows an atrial pulse generator 2022 and a ventricular pulse generator 2024 that generate pacing stimulation pulses for delivery by the right atrial lead 1904, the coronary sinus lead 1906, the right ventricular lead 1908, or some combination of these leads via an electrode configuration switch 2026. It is understood that in order to provide stimulation therapy in each of the four chambers of the heart, the atrial and ventricular pulse generators 2022 and 2024 may include dedicated, independent pulse generators, multiplexed pulse generators, or shared pulse generators. The pulse generators 2022 and 2024 are controlled by the microcontroller 2020 via appropriate control signals 2028 and 2030, respectively, to trigger or inhibit the stimulation pulses.

Microcontroller 2020 further includes timing control circuitry 2032 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 2020 further includes an arrhythmia detector 2034. The arrhythmia detector 2034 may be utilized by the device 1900 for determining desirable times to administer various therapies. The arrhythmia detector 2034 may be implemented, for example, in hardware as part of the microcontroller 2020, or as software/firmware instructions programmed into the device 1900 and executed on the microcontroller 2020 during certain modes of operation.

Microcontroller 2020 may include a morphology discrimination module 2036, a capture detection module (not shown) and an auto sensing module (not shown). These modules are optionally used to implement various exemplary recognition algorithms or methods. The aforementioned components may be implemented, for example, in hardware as part of the microcontroller 2020, or as software/firmware instructions programmed into the device 1900 and executed on the microcontroller 2020 during certain modes of operation.

The electrode configuration switch 2026 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 2026, in response to a control signal 2042 from the microcontroller 2020, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 2044 and ventricular sensing circuits (VTR. SENSE) 2046 may also be selectively coupled to the right atrial lead 1904, coronary sinus lead 1906, and the right ventricular lead 1908, through the switch 2026 for detecting the presence of cardiac activity in each of the four chambers of the heart. Accordingly, the atrial and ventricular sensing circuits 2044 and 2046 may include dedicated sense amplifiers, multiplexed amplifiers, or shared amplifiers. Switch 2026 determines the "sensing polarity" of the cardiac signal by selectively closing the appropriate switches, as is also known in the art. In this way, the clinician may program the sensing polarity independent of the stimulation polarity. The sensing circuits (e.g., circuits 2044 and 2046) are optionally capable of obtaining information indicative of tissue capture.

Each sensing circuit 2044 and 2046 preferably employs one or more low power, precision amplifiers with programmable gain, automatic gain control, bandpass filtering, a threshold detection circuit, or some combination of these components, to selectively sense the cardiac signal of interest. The automatic gain control enables the device 1900 to deal effectively with the difficult problem of sensing the low amplitude signal characteristics of atrial or ventricular fibrillation.

The outputs of the atrial and ventricular sensing circuits 2044 and 2046 are connected to the microcontroller 2020, which, in turn, is able to trigger or inhibit the atrial and ventricular pulse generators 2022 and 2024, respectively, in a demand fashion in response to the absence or presence of cardiac activity in the appropriate chambers of the heart. Furthermore, as described herein, the microcontroller 2020 is also capable of analyzing information output from the sensing circuits 2044 and 2046, a data acquisition system 2052, or both. This information may be used to determine or detect whether and to what degree tissue capture has occurred and to program a pulse, or pulses, in response to such determinations. The sensing circuits 2044 and 2046, in turn, receive control signals over signal lines 2048 and 2050, respectively, from the microcontroller 2020 for purposes of controlling the gain, threshold, polarization charge removal circuitry (not shown), and the timing of any blocking circuitry (not shown) coupled to the inputs of the sensing circuits 2044 and 2046 as is known in the art.

For arrhythmia detection, the device 1900 utilizes the atrial and ventricular sensing circuits 2044 and 2046 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 2034 of the microcontroller 2020 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 2052. The data acquisition system 2052 is configured (e.g., via signal line 2056) to acquire intracardiac electrogram ("IEGM") signals or other signals, convert the raw analog data into a digital signal, and store the digital signals for later processing, for telemetric transmission to an external device 2054, or both. For example, the data acquisition system 2052 may be coupled to the right atrial lead 1904, the coronary sinus lead 1906, the right ventricular lead 1908 and other leads through the switch 2026 to sample cardiac signals across any pair of desired electrodes.

The data acquisition system 2052 also may be coupled to receive signals from other input devices. For example, the data acquisition system 2052 may sample signals from a physiologic sensor 2070 or other components shown in FIG. 20 (connections not shown).

The microcontroller 2020 is further coupled to a memory 2060 by a suitable data/address bus 2062, wherein the programmable operating parameters used by the microcontroller 2020 are stored and modified, as required, in order to customize the operation of the device 1900 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 2052), which data may then be used for subsequent analysis to guide the programming of the device 1900.

Advantageously, the operating parameters of the implantable device 1900 may be non-invasively programmed into the memory 2060 through a telemetry circuit 2064 in telemetric communication via communication link 2066 with the external device 2054, such as a programmer, transtelephonic transceiver, a diagnostic system analyzer or some other device. The microcontroller 2020 activates the telemetry circuit 2064 with a control signal (e.g., via bus 2068). The telemetry circuit 2064 advantageously allows intracardiac electrograms and status information relating to the operation of the device 1900 (as contained in the microcontroller 2020 or memory 2060) to be sent to the external device 2054 through an established communication link 2066.

The device 1900 can further include one or more physiologic sensors 2070. In some embodiments the device 1900 may include a "rate-responsive" sensor that may provide, for example, information to aid in adjustment of pacing stimulation rate according to the exercise state of the patient. One or more physiologic sensors 2070 (e.g., a pressure sensor) may further be used to detect changes in cardiac output, changes in the physiological condition of the heart, or diurnal changes in activity (e.g., detecting sleep and wake states). Accordingly, the microcontroller 2020 responds by adjusting the various pacing parameters (such as rate, AV Delay, V-V Delay, etc.) at which the atrial and ventricular pulse generators 2022 and 2024 generate stimulation pulses.

While shown as being included within the device 1900, it is to be understood that a physiologic sensor 2070 may also be external to the device 1900, yet still be implanted within or carried by the patient. Examples of physiologic sensors that may be implemented in conjunction with the device 1900 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors 2070 may optionally include one or more of components to help detect movement (via, e.g., a position sensor or an accelerometer) and minute ventilation (via an MV sensor) in the patient. Signals generated by the position sensor and MV sensor may be passed to the microcontroller 2020 for analysis in determining whether to adjust the pacing rate, etc. The microcontroller 2020 may thus monitor the signals for indications of the patient's position and activity status, such as whether the patient is climbing up stairs or descending down stairs or whether the patient is sitting up after lying down.

The device 1900 additionally includes a battery 2076 that provides operating power to all of the circuits shown in FIG. 20. For a device 1900 which employs shocking therapy, the battery 2076 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 2076 also desirably has a predictable discharge characteristic so that elective replacement time can be detected. Accordingly, the device 1900 preferably employs lithium or other suitable battery technology.

The device 1900 can further include magnet detection circuitry (not shown), coupled to the microcontroller 2020, to detect when a magnet is placed over the device 1900. A magnet may be used by a clinician to perform various test functions of the device 1900 and to signal the microcontroller 2020 that the external device 2054 is in place to receive data from or transmit data to the microcontroller 2020 through the telemetry circuit 2064.

The device 1900 further includes an impedance measuring circuit 2078 that is enabled by the microcontroller 2020 via a control signal 2080. The known uses for an impedance measuring circuit 2078 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 1900 has been implanted; measuring stroke volume; and detecting the opening of heart valves, etc. The impedance measuring circuit 2078 is advantageously coupled to the switch 2026 so that any desired electrode may be used.

In the case where the device 1900 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 2020 further controls a shocking circuit 2082 by way of a control signal 2084. The shocking circuit 2082 generates shocking pulses of low (e.g., up to 0.5 J), moderate (e.g., 0.5 J to 10 J), or high energy (e.g., 11 J to 40 J), as controlled by the microcontroller 2020. Such shocking pulses are applied to the patient's heart H through, for example, two shocking electrodes and as shown in this embodiment, selected from the left atrial coil electrode 1926, the RV coil electrode 1932 and the SVC coil electrode 1934. As noted above, the housing 2000 may act as an active electrode in combination with the RV coil electrode 1932, as part of a split electrical vector using the SVC coil electrode 1934 or the left atrial coil electrode 1926 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 2020 is capable of controlling the synchronous or asynchronous delivery of the shocking pulses.

As mentioned above, a device such as the device 1900 may include several components that provide shape discrimination functionality as taught herein. For example, one or more of the switch 2026, the sense circuits 2044 and 2046, the impedance measuring circuit 2078, the physiologic sensors 2070, and the data acquisition system 2052 may acquire cardiac signals that are used in the operations discussed above. The vector and matrix information described above may be stored in the data memory 2060. In addition, a warning/therapy module 2040 may be configured to generate warning signals and facilitate the administration of therapy.

The microcontroller 2020 (e.g., a processor providing signal processing functionality) also may implement or support at least a portion of the functionality discussed herein. For example, an IEGM module 2039 may be used to provide and analyze electrocardiogram signals (e.g., waveforms). A vector generator component 2038 may provide and process vectors or similar data (e.g., shape vectors and ranking vectors). A matrix generator component 2037 may provide and process one or more matrices or similar data (e.g., a score matrix). The morphology discrimination module 2036 may provide discrimination-related functionality. The arrhythmia detector 2034 may provide indications of arrhythmia (e.g., tachycardia) and provide other processing relating to the identification of arrhythmias. The timing control module 2032 may provide functionality relating to, for example, determining when to acquire cardiac information.

It should be appreciated that various modifications may be incorporated into the disclosed embodiments based on the teachings herein. For example, the structure and functionality taught herein may be incorporated into types of devices other than the specific types of devices described above. In addition, different rules may be employed to define a matrix or any of the vectors described above. Different techniques may be use to identify preferred alignments and different tests may be used to score a vector using a matrix. Also, various algorithms or techniques may be employed to obtain and process information relating to inflection points of a cardiac waveform. For example, other techniques may be employed to provide baseline information (e.g., information indicative of inflection points) and to provide the information that is compared against the baseline information to identify a particular condition. Furthermore, information relating to inflection points may be used in a variety of ways to characterize or otherwise identify one or more cardiac conditions associated with underlying cardiac waveforms. For example, morphology discrimination as taught herein may be employed to identify cardiac waveforms that are collected at times when a patient is not in sinus or is not experiencing a tachycardia arrhythmia. Also, the shape recognition techniques taught herein may be applicable to a variety of fields that involve shape analysis, and are not limited to analysis of cardiac signals.

It should be appreciated from the above that the various structures and functions described herein may be incorporated into a variety of apparatuses (e.g., a stimulation device, a lead, a monitoring device, etc.) and implemented in a variety of ways. Different embodiments of such an apparatus may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to an element herein using a designation such as "first," "second," and so forth does not generally limit the quantity or order of those elements. Rather, these designations are used herein as a convenient method of distinguishing between two or more different nodes. Thus, a reference to first and second sets does not mean that only two sets may be employed there or that the first set must precede the second set in some manner. Also, unless stated otherwise a set of elements may comprise one or more elements.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad inventive scope thereof. In view of the above it will be understood that the teachings herein are intended to cover any changes, adaptations or modifications which are within the scope of the disclosure as defined by any claims associated herewith.

What is claimed is:

1. A method of processing cardiac signals, comprising:
   acquiring cardiac signals;
   generating a derivative of the acquired cardiac signals;
   performing morphology discrimination based on inflection points of the derivative of the acquired cardiac signals; and
   identifying, based on the morphology discrimination, a cardiac condition associated with at least a portion of the cardiac signals, wherein:
      the acquired cardiac signals comprise a baseline set of cardiac signals; and wherein;
      performing morphology discrimination comprises generating baseline information based on inflection points of the derivative of the baseline set of cardiac signals;
      the generation of the baseline information comprises processing the derivative of the baseline set of cardiac signals to generate a first set of shape vectors;
      the acquired cardiac signals further comprise a second set of cardiac signals;
      the derivative of the second set of cardiac signals are processed to generate a second set of shape vectors; and
      performing morphology discrimination further comprises scoring the second set of shape vectors using the baseline information.

2. The method of claim 1, wherein identifying the cardiac condition comprises distinguishing between ventricular tachycardia and super-ventricular tachycardia.

3. The method of claim 1, wherein the baseline information relates to a shape distribution of the patient's normal sinus rhythm.

4. The method of claim 1, wherein the acquired cardiac signals further comprise a second set of cardiac signals and wherein performing morphology discrimination further comprises comparing the baseline information with information based on inflection points of the derivative of the second set of cardiac signals.

5. The method of claim 1, wherein the generation of the baseline information further comprises:
   defining an upper bound and a lower bound for each column of a matrix;
   comparing elements of each shape vector of the first set of shape vectors with the upper and lower bounds to determine how to align the matrix with each shape vector of the first set of shape vectors; and
   incorporating information into the matrix by incrementing a count relating to magnitude and relative position of each element of each shape vector of the first set of shape vectors.

6. The method of claim 5, further comprising identifying a set of potential alignments of the matrix with each shape vector of the first set of shape vectors based on whether each of the potential alignments would result in an increase in a quantity of columns of the matrix.

7. The method of claim 5, wherein the morphology discrimination further comprises:
   defining a core of the matrix;
   aligning each shape vector of the second set of shape vectors with the core of the matrix;
   determining a weight associated with each of the aligned shape vectors based on a count of how many times a magnitude associated with one or more elements of the aligned shape vectors has been added to a corresponding column of the matrix; and
   summing the weights to generate a score indicative of a degree of similarity between the matrix and the second set of shape vectors.

8. A method of processing cardiac signals, comprising:
   acquiring cardiac signals comprising a baseline set of cardiac signals and a second set of cardiac signals;
   performing morphology discrimination based on inflection points of the acquired cardiac signals, comprising:
      generating baseline information based on inflection points of the baseline set of acquired cardiac signals, wherein generating baseline information comprises:
         processing the baseline set of cardiac signals to generate a first set of shape vectors;
         defining an upper bound and a lower bound for each column of a matrix;
         comparing elements of each shape vector of the first set of shape vectors with the upper and lower bounds to determine how to align the matrix with each shape vector of the first set of shape vectors; and
         incorporating information into the matrix by incrementing a count relating to magnitude and relative position of each element of each shape vector of the first set of shape vectors;
      processing the second set of cardiac signals to generate a second set of shape vectors; and
      scoring the second set of shape vectors using the baseline information; and identifying, based on the morphology discrimination, a cardiac condition associated with at least a portion of the cardiac signals.

9. The method of claim 8, further comprising identifying a set of potential alignments of the matrix with each shape vector of the first set of shape vectors based on whether each of the potential alignments would result in an increase in a quantity of columns of the matrix.

10. The method of claim 8, wherein the morphology discrimination further comprises:
defining a core of the matrix;
aligning each shape vector of the second set of shape vectors with the core of the matrix;
determining a weight associated with each of the aligned shape vectors based on a count of how many times a magnitude associated with one or more elements of the aligned shape vectors has been added to a corresponding column of the matrix; and
summing the weights to generate a score indicative of a degree of similarity between the matrix and the second set of shape vectors.

11. A non-transitory computer readable medium having instructions that when executed on a processor of an implantable medical device (IMD) having cardiac pacing capabilities cause the IMD to:
acquire cardiac signals;
generate a derivative of the acquired cardiac signals;
perform morphology discrimination based on inflection points of the derivative of the acquired cardiac signals; and
identify, based on the morphology discrimination, a cardiac condition associated with at least a portion of the cardiac signals, wherein:
the acquired cardiac signals comprise a baseline set of cardiac signals;
performing morphology discrimination comprises generating baseline information based on inflection points of the derivative of the baseline set of cardiac signals;
the generation of the baseline information comprises processing the derivative of the baseline set of cardiac signals to generate a first set of shape vectors;
the acquired cardiac signals further comprise a second set of cardiac signals;
the derivative of the second set of cardiac signals are processed to generate a second set of shape vectors; and performing morphology discrimination further comprises scoring the second set of shape vectors using the baseline information.

12. The computer readable medium of claim 11, wherein identifying the cardiac condition comprises distinguishing between ventricular tachycardia and super-ventricular tachycardia.

13. The computer readable medium of claim 11, wherein the baseline information relates to a shape distribution of the patient's normal sinus rhythm.

14. The computer readable medium of claim 11, wherein the acquired cardiac signals further comprise a second set of cardiac signals and wherein performing morphology discrimination further comprises comparing the baseline information with information based on inflection points of the derivative of the second set of cardiac signals.

15. The computer readable medium of claim 11, wherein the generation of the baseline information further comprises:
defining an upper bound and a lower bound for each column of a matrix;
comparing elements of each shape vector of the first set of shape vectors with the upper and lower bounds to determine how to align the matrix with each shape vector of the first set of shape vectors; and
incorporating information into the matrix by incrementing a count relating to magnitude and relative position of each element of each shape vector of the first set of shape vectors.

16. The computer readable medium of claim 15, wherein the instruction further cause the processor to: identify a set of potential alignments of the matrix with each shape vector of the first set of shape vectors based on whether each of the potential alignments would result in an increase in a quantity of columns of the matrix.

17. The computer readable medium of claim 15, wherein the morphology discrimination further comprises:
defining a core of the matrix;
aligning each shape vector of the second set of shape vectors with the core of the matrix;
determining a weight associated with each of the aligned shape vectors based on a count of how many times a magnitude associated with one or more elements of the aligned shape vectors has been added to a corresponding column of the matrix; and
summing the weights to generate a score indicative of a degree of similarity between the matrix and the second set of shape vectors.

* * * * *